(12) United States Patent
Van Der Oost et al.

(10) Patent No.: US 11,802,277 B2
(45) Date of Patent: *Oct. 31, 2023

(54) THERMOSTABLE CAS9 NUCLEASES

(71) Applicant: Wageningen Universiteit, Wageningen (NL)

(72) Inventors: John Van Der Oost, Renkum (NL); Martinus Johannes Arnoldus Daas, Huissen (NL); Servatius Wilhelmus Maria Kengen, Beuningen (NL); Willem Meindert De Vos, Ede (NL)

(73) Assignee: Wageningen Universiteit, Wageningen (NL)

( * ) Notice: Subject to any disclaimer, the term of this patent is extended or adjusted under 35 U.S.C. 154(b) by 286 days.

This patent is subject to a terminal disclaimer.

(21) Appl. No.: 16/906,741

(22) Filed: Jun. 19, 2020

(65) Prior Publication Data

US 2020/0385697 A1 Dec. 10, 2020

Related U.S. Application Data

(63) Continuation of application No. 15/735,359, filed as application No. PCT/EP2016/062817 on Jun. 6, 2016, now Pat. No. 10,731,142.

(30) Foreign Application Priority Data

Jun. 12, 2015 (GB) .................................... 1510296

(51) Int. Cl.
*C12N 9/22* (2006.01)
*C12N 15/79* (2006.01)

(52) U.S. Cl.
CPC ............... *C12N 9/22* (2013.01); *C12N 15/79* (2013.01); *C12N 2310/20* (2017.05); *C12Y 301/21* (2013.01)

(58) Field of Classification Search
CPC ...... C12N 15/633; C12N 15/79; C12N 15/85; C12N 2310/20; C12N 9/00; C12N 9/22; C12Y 301/21
See application file for complete search history.

(56) References Cited

U.S. PATENT DOCUMENTS

| 10,731,142 | B2 * | 8/2020 | Van Der Oost | ........ | C12N 15/79 |
| 11,242,513 | B2 * | 2/2022 | Van Der Oost | ...... | C12N 15/102 |
| 11,326,162 | B2 * | 5/2022 | Van Der Oost | .......... | C12N 9/22 |
| 2011/0217739 | A1 * | 9/2011 | Terns | ...................... | C12N 9/22 |
| | | | | | 435/243 |
| 2014/0068797 | A1 * | 3/2014 | Doudna | ............... | A01H 6/4684 |
| | | | | | 435/375 |
| 2017/0360048 | A1 * | 12/2017 | Nunez | ...................... | C12N 15/66 |

FOREIGN PATENT DOCUMENTS

WO 2013176772 11/2013

OTHER PUBLICATIONS

V6VHM9_9BACI (Feb. 19, 2014).*
S5ZZV3_BACPJ (Oct. 16, 2013).*
Kermekchiev et al, Cold-sensitive mutants of Taq DNA polymerase provide a hot start for PCR, Nucleic Acids Res. 31(21): 6139-6147, 2003.*
Notice of Allowance for U.S. Appl. No. 15/735,359, dated Jun. 26, 2020, 6 pages.
"Bacillus smithii CRISPR polypeptide SEQ: 816.", Geneseq, (Jan. 16, 2014), Database accession No. BAZ50353, URL: EBI, XP002760959, 1 page.
Gilbert et al. "CRISPR-Mediated Modular RNA-Guided Regulation of Transcription in Eukaryotes", Cell (2013) vol. 154, pp. 442-451.
Filippidou et al., GenBank accession KJE28390, Mar. 5, 2015, 1 page.
Chylinski Krzysztof et al, "Classification and evolution of type II CRISPR-Cas systems", Nucleic Acids Research, vol. 42, Issue 10, Jun. 2, 2014, pp. 6091-6105.
Doolittle et al, "On the origin of prokaryotic species," Genome Res. 19: 744-756, 2009.
He et al, "The kinetics of thermal injury in human renal carcinoma cells," Ann. Biomed. Eng. Apr. 2005;33(4): pp. 502-510.
Moats, "Kinetics of thermal death of bacteria," J. Bacteriol. Jan. 1971;105(1): pp. 165-171.
Mougiakos et al., "Characterizing a thermostable Cas9 for bacterial genome editing and silencing," Nature Communications, Nov. 21, 2017;8(1): pp. 1-11.

(Continued)

*Primary Examiner* — Kevin K Hill
(74) *Attorney, Agent, or Firm* — Riverside Law LLP

(57) ABSTRACT

Thermostable Cas9 nucleases. The present invention relates to the field of genetic engineering and more particularly to nucleic acid editing and genome modification. The present invention provides in isolated Cas protein or polypeptide fragment thereof having an amino acid sequence of SEQ ID NO: 1 or a sequence of at least 77% identity therewith, wherein the Cas protein or polypeptide is capable of DNA cleavage at a temperature in the range 50° C. and 100° C. inclusive. The invention further provides isolated nucleic acid molecules encoding said Cas9 nucleases, expression vectors and host cells. The Cas9 nucleases disclosed herein provide novel tools for genetic engineering at elevated temperatures and are of particular value in the genetic manipulation of thermophilic organisms; particularly microorganisms.

21 Claims, 8 Drawing Sheets

Specification includes a Sequence Listing.

(56) References Cited

OTHER PUBLICATIONS

Siddiq M.A., Rashid N., Whittman W., Ayyampalayam S.; "Complete Genome Sequence of Geobacillus thermopakistaniensis MAS1."; EMBL/GenBank/DDBJ databases; V6VHM9_9BACI; integrated into UniProtKB/TrEMBL, Feb. 19, 2014, 1 page.
Siddiqui Masood Ahmed et al, "Draft Genome Sequence of Geobacillus thermopakistaniensis Strain MAS1.", Genome Announcements, Jun. 5, 2014;2(3):e00559-14, 1 page.
Sweetlove, L. "Number of species on Earth tagged at 8.7 million." Nature (Aug. 3, 2011), 1 page.

* cited by examiner

Fig. 3 (continued)

```
                            SEQUENCE LISTING

<160> NUMBER OF SEQ ID NOS: 9

<210> SEQ ID NO 1
<211> LENGTH: 1082
<212> TYPE: PRT
<213> ORGANISM: Geobacillus thermodenitrificans T12

<400> SEQUENCE: 1

Met Lys Tyr Lys Ile Gly Leu Asp Ile Gly Ile Thr Ser Ile Gly Trp
1               5                   10                  15

Ala Val Ile Asn Leu Asp Ile Pro Arg Ile Glu Asp Leu Gly Val Arg
            20                  25                  30

Ile Phe Asp Arg Ala Glu Asn Pro Lys Thr Gly Glu Ser Leu Ala Leu
        35                  40                  45

Pro Arg Arg Leu Ala Arg Ser Ala Arg Arg Arg Leu Arg Arg Arg Lys
    50                  55                  60

His Arg Leu Glu Arg Ile Arg Arg Leu Phe Val Arg Glu Gly Ile Leu
65                  70                  75                  80

Thr Lys Glu Glu Leu Asn Lys Leu Phe Glu Lys Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Ile Leu Leu His Leu Ala Lys Arg Arg Gly Phe Arg
        115                 120                 125

Ser Asn Arg Lys Ser Glu Arg Thr Asn Lys Glu Asn Ser Thr Met Leu
    130                 135                 140

Lys His Ile Glu Glu Asn Gln Ser Ile Leu Ser Ser Tyr Arg Thr Val
145                 150                 155                 160

Ala Glu Met Val Val Lys Asp Pro Lys Phe Ser Leu His Lys Arg Asn
                165                 170                 175

Lys Glu Asp Asn Tyr Thr Asn Thr Val Ala Arg Asp Asp Leu Glu Arg
            180                 185                 190

Glu Ile Lys Leu Ile Phe Ala Lys Gln Arg Glu Tyr Gly Asn Ile Val
        195                 200                 205

Cys Thr Glu Ala Phe Glu His Glu Tyr Ile Ser Ile Trp Ala Ser Gln
    210                 215                 220

Arg Pro Phe Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255

Gln Ser Phe Thr Val Trp Glu His Ile Asn Lys Leu Arg Leu Val Ser
            260                 265                 270

Pro Gly Gly Ile Arg Ala Leu Thr Asp Asp Glu Arg Arg Leu Ile Tyr
        275                 280                 285

Lys Gln Ala Phe His Lys Asn Lys Ile Thr Phe His Asp Val Arg Thr
    290                 295                 300

Leu Leu Asn Leu Pro Asp Asp Thr Arg Phe Lys Gly Leu Leu Tyr Asp
305                 310                 315                 320

Arg Asn Thr Thr Leu Lys Glu Asn Glu Lys Val Arg Phe Leu Glu Leu
                325                 330                 335
```

```
Gly Ala Tyr His Lys Ile Arg Lys Ala Ile Asp Ser Val Tyr Gly Lys
            340                 345                 350

Gly Ala Ala Lys Ser Phe Arg Pro Ile Asp Phe Asp Thr Phe Gly Tyr
        355                 360                 365

Ala Leu Thr Met Phe Lys Asp Asp Thr Asp Ile Arg Ser Tyr Leu Arg
    370                 375                 380

Asn Glu Tyr Glu Gln Asn Gly Lys Arg Met Glu Asn Leu Ala Asp Lys
385                 390                 395                 400

Val Tyr Asp Glu Glu Leu Ile Glu Glu Leu Leu Asn Leu Ser Phe Ser
                405                 410                 415

Lys Phe Gly His Leu Ser Leu Lys Ala Leu Arg Asn Ile Leu Pro Tyr
            420                 425                 430

Met Glu Gln Gly Glu Val Tyr Ser Thr Ala Cys Glu Arg Ala Gly Tyr
        435                 440                 445

Thr Phe Thr Gly Pro Lys Lys Lys Gln Lys Thr Val Leu Leu Pro Asn
    450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Glu Leu Ser Gln Ser Phe Asp Glu Arg
            500                 505                 510

Arg Lys Met Gln Lys Glu Gln Glu Gly Asn Arg Lys Lys Asn Glu Thr
        515                 520                 525

Ala Ile Arg Gln Leu Val Glu Tyr Gly Leu Thr Leu Asn Pro Thr Gly
    530                 535                 540

Leu Asp Ile Val Lys Phe Lys Leu Trp Ser Glu Gln Asn Gly Lys Cys
545                 550                 555                 560

Ala Tyr Ser Leu Gln Pro Ile Glu Ile Glu Arg Leu Leu Glu Pro Gly
                565                 570                 575

Tyr Thr Glu Val Asp His Val Ile Pro Tyr Ser Arg Ser Leu Asp Asp
            580                 585                 590

Ser Tyr Thr Asn Lys Val Leu Val Leu Thr Lys Glu Asn Arg Glu Lys
        595                 600                 605

Gly Asn Arg Thr Pro Ala Glu Tyr Leu Gly Leu Gly Ser Glu Arg Trp
    610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Asn
                645                 650                 655

Glu Phe Lys Asn Arg Asn Leu Asn Asp Thr Arg Tyr Ile Ser Arg Phe
            660                 665                 670

Leu Ala Asn Phe Ile Arg Glu His Leu Lys Phe Ala Asp Ser Asp Asp
        675                 680                 685

Lys Gln Lys Val Tyr Thr Val Asn Gly Arg Ile Thr Ala His Leu Arg
    690                 695                 700

Ser Arg Trp Asn Phe Asn Lys Asn Arg Glu Glu Ser Asn Leu His His
705                 710                 715                 720

Ala Val Asp Ala Ala Ile Val Ala Cys Thr Thr Pro Ser Asp Ile Ala
                725                 730                 735

Arg Val Thr Ala Phe Tyr Gln Arg Arg Glu Gln Asn Lys Glu Leu Ser
            740                 745                 750

Lys Lys Thr Asp Pro Gln Phe Pro Gln Pro Trp Pro His Phe Ala Asp
```

```
                755                 760                 765
Glu Leu Gln Ala Arg Leu Ser Lys Asn Pro Lys Glu Ser Ile Lys Ala
    770                 775                 780
Leu Asn Leu Gly Asn Tyr Asp Asn Glu Lys Leu Glu Ser Leu Gln Pro
785                 790                 795                 800
Val Phe Val Ser Arg Met Pro Lys Arg Ser Ile Thr Gly Ala Ala His
                805                 810                 815
Gln Glu Thr Leu Arg Arg Tyr Ile Gly Ile Asp Glu Arg Ser Gly Lys
            820                 825                 830
Ile Gln Thr Val Val Lys Lys Leu Ser Glu Ile Gln Leu Asp Lys
            835                 840                 845
Thr Gly His Phe Pro Met Tyr Gly Lys Glu Ser Asp Pro Arg Thr Tyr
    850                 855                 860
Glu Ala Ile Arg Gln Arg Leu Leu Glu His Asn Asn Asp Pro Lys Lys
865                 870                 875                 880
Ala Phe Gln Glu Pro Leu Tyr Lys Pro Lys Lys Asn Gly Glu Leu Gly
                885                 890                 895
Pro Ile Ile Arg Thr Ile Lys Ile Ile Asp Thr Thr Asn Gln Val Ile
            900                 905                 910
Pro Leu Asn Asp Gly Lys Thr Val Ala Tyr Asn Ser Asn Ile Val Arg
        915                 920                 925
Val Asp Val Phe Glu Lys Asp Gly Lys Tyr Tyr Cys Val Pro Ile Tyr
930                 935                 940
Thr Ile Asp Met Met Lys Gly Ile Leu Pro Asn Lys Ala Ile Glu Pro
945                 950                 955                 960
Asn Lys Pro Tyr Ser Glu Trp Lys Glu Met Thr Glu Asp Tyr Thr Phe
                965                 970                 975
Arg Phe Ser Leu Tyr Pro Asn Asp Leu Ile Arg Ile Glu Phe Pro Arg
            980                 985                 990
Glu Lys Thr Ile Lys Thr Ala Val Gly Glu Glu Ile Lys Ile Lys Asp
        995                 1000                1005
Leu Phe Ala Tyr Tyr Gln Thr Ile Asp Ser Ser Asn Gly Gly Leu
    1010                1015                1020
Ser Leu Val Ser His Asp Asn Asn Phe Ser Leu Arg Ser Ile Gly
    1025                1030                1035
Ser Arg Thr Leu Lys Arg Phe Glu Lys Tyr Gln Val Asp Val Leu
    1040                1045                1050
Gly Asn Ile Tyr Lys Val Arg Gly Glu Lys Arg Val Gly Val Ala
    1055                1060                1065
Ser Ser Ser His Ser Lys Ala Gly Glu Thr Ile Arg Pro Leu
    1070                1075                1080

<210> SEQ ID NO 2
<211> LENGTH: 8
<212> TYPE: PRT
<213> ORGANISM: Geobacillus thermodenitrificans T12

<400> SEQUENCE: 2

Glu Lys Asp Gly Lys Tyr Tyr Cys
1               5

<210> SEQ ID NO 3
<211> LENGTH: 6
<212> TYPE: PRT
<213> ORGANISM: Artificial Sequence
<220> FEATURE:
```

```
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Ile, Met or Pro
<220> FEATURE:
<221> NAME/KEY: misc_feature
<222> LOCATION: (2)..(2)
<223> OTHER INFORMATION: Xaa can be any of Val, Ser, Asn or Ile
<220> FEATURE:
<221> NAME/KEY: misc_feature
<222> LOCATION: (5)..(5)
<223> OTHER INFORMATION: Xaa can be any of Glu or Lys
<220> FEATURE:
<221> NAME/KEY: misc_feature
<222> LOCATION: (6)..(6)
<223> OTHER INFORMATION: Xaa can be any of Ala, Glu or Arg

<400> SEQUENCE: 3

Xaa Xaa Cys Thr Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Met or Phe
<220> FEATURE:
<221> NAME/KEY: misc_feature
<222> LOCATION: (4)..(4)
<223> OTHER INFORMATION: Xaa can be any of His or Asn

<400> SEQUENCE: 4

Xaa Leu Lys Xaa Ile Glu
1               5

<210> SEQ ID NO 5
<211> LENGTH: 6
<212> TYPE: PRT
<213> ORGANISM: Artificial Sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Glu or Ile
<220> FEATURE:
<221> NAME/KEY: misc_feature
<222> LOCATION: (5)..(5)
<223> OTHER INFORMATION: Xaa can be any of Trp, Ser or Lys

<400> SEQUENCE: 5

Xaa Val Tyr Ser Xaa Lys
1               5

<210> SEQ ID NO 6
<211> LENGTH: 12
<212> TYPE: PRT
<213> ORGANISM: Artificial sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Ala or Glu
<220> FEATURE:
<221> NAME/KEY: misc_feature
<222> LOCATION: (4)..(4)
```

```
<223> OTHER INFORMATION: Xaa can be any of Gln or Lys
<220> FEATURE:
<221> NAME/KEY: misc_feature
<222> LOCATION: (5)..(5)
<223> OTHER INFORMATION: Xaa can be any of Arg or Ala
<220> FEATURE:
<221> NAME/KEY: misc_feature
<222> LOCATION: (9)..(9)
<223> OTHER INFORMATION: Xaa can be any of Asn or Ala
<220> FEATURE:
<221> NAME/KEY: misc_feature
<222> LOCATION: (12)..(12)
<223> OTHER INFORMATION: Xaa can be any of Lys or Ser

<400> SEQUENCE: 6

Xaa Phe Tyr Xaa Xaa Arg Glu Gln Xaa Lys Glu Xaa
1               5                   10

<210> SEQ ID NO 7
<211> LENGTH: 3249
<212> TYPE: DNA
<213> ORGANISM: Geobacillus thermodenitrificans T12

<400> SEQUENCE: 7
atgaagtata aaatcggtct tgatatcggc attacgtcta tcggttgggc tgtcattaat      60
ttggacattc ctcgcatcga agatttaggt gtccgcattt ttgacagagc ggaaaacccg     120
aaaaccgggg agtcactagc tcttccacgt cgcctcgccc gctccgcccg acgtcgtctg     180
cggcgtcgca acatcgact ggagcgcatt cgccgcctgt tcgtccgcga aggaattta      240 acgaaggaag agctgaacaa gctgtttgaa aaaaagcacg aaatcgacgt ctggcagctt     300
cgtgttgaag cactggatcg aaaactaaat aacgatgaat tagcccgcat ccttcttcat     360
ctggctaaac ggcgtggatt tagatccaac cgcaagagtg agcgcaccaa caaagaaaac     420
agtacgatgc tcaaacatat tgaagaaaac caatccattc tttcaagtta ccgaacggtt     480
gcagaaatgg ttgtcaagga tccgaaattt tccctgcaca gcgtaataaa gaggataat      540 tacaccaaca ctgttgcccg cgacgatctt gaacgggaaa tcaaactgat tttcgccaaa     600
cagcgcgaat atgggaacat cgtttgcaca gaagcatttg aacacgagta tatttccatt     660
tgggcatcgc aacgcccttt tgcttctaag gatgatatcg agaaaaagt cggtttctgt      720 acgtttgagc ctaagaaaaa acgcgcgcca aaagcaacat acacattcca gtccttcacc     780
gtctgggaac atattaacaa acttcgtctt gtctccccgg gaggcatccg ggcactaacc     840
gatgatgaac gtcgtcttat atacaagcaa gcatttcata aaaataaaat caccttccat     900
gatgttcgaa cattgcttaa cttgcctgac gacacccgtt ttaaaggtct tttatatgac     960
cgaaacacca cgctgaagga aaatgagaaa gttcgcttcc ttgaactcgg cgcctatcat    1020
aaaatacgga aagcgatcga cagcgtctat ggcaaaggag cagcaaaatc atttcgtccg    1080
attgattttg atacatttgg ctacgcatta acgatgttta agacgacac cgacattcgc    1140 agttacttgc gaaacgaata cgaacaaaat ggaaaacgaa tggaaaatct agcggataaa    1200
gtctatgatg aagaattgat tgaagaactt ttaaacttat cgttttctaa gtttggtcat    1260
ctatccctta aagcgcttcg caacatcctt ccatatatgg aacaaggcga agtctactca    1320
accgcttgtg aacgagcagg atatacattt acagggccaa agaaaaaaca gaaaacggta    1380
ttgctgccga acattccgcc gatcgccaat ccggtcgtca tgcgcgcact gacacaggca    1440
cgcaaagtgg tcaatgccat tatcaaaaag tacggctcac cggtctccat ccatatcgaa    1500
ctggcccggg aactatcaca atccctttgat gaacgacgta aaatgcagaa agaacaggaa    1560
```

```
ggaaaccgaa agaaaaacga aactgccatt cgccaacttg ttgaatatgg gctgacgctc    1620
aatccaactg ggcttgacat tgtgaaattc aaactatgga gcgaacaaaa cggaaaatgt    1680
gcctattcac tccaaccgat cgaaatcgag cggttgctcg aaccaggcta tacagaagtc    1740
gaccatgtga ttccatacag ccgaagcttg gacgatagct ataccaataa agttcttgtg    1800
ttgacaaagg agaaccgtga aaaggaaac cgcaccccag ctgaatattt aggattaggc    1860
tcagaacgtt ggcaacagtt cgagacgttt gtcttgacaa ataagcagtt ttcgaaaaag    1920
aagcgggatc gactccttcg gcttcattac gatgaaaacg aagaaatga gtttaaaaat    1980
cgtaatctaa atgataccg ttatatctca cgcttcttgg ctaactttat tcgcgaacat    2040
ctcaaattcg ccgacagcga tgacaaacaa aaagtataca cggtcaacgg ccgtattacc    2100
gcccatttac gcagccgttg gaattttaac aaaaaccggg aagaatcgaa tttgcatcat    2160
gccgtcgatg ctgccatcgt cgcctgcaca acgccgagcg atatcgcccg agtcaccgcc    2220
ttctatcaac ggcgcgaaca aaacaaagaa ctgtccaaaa agacggatcc gcagtttccg    2280
cagccttggc cgcactttgc tgatgaactg caggcgcgtt tatcaaaaaa tccaaaggag    2340
agtataaaag ctctcaatct tggaaattat gataacgaga actcgaatc gttgcagccg    2400
gttttttgtct cccgaatgcc gaagcggagc ataacaggag cggctcatca gaaacattg    2460
cggcgttata tcggcatcga cgaacggagc ggaaaaatac agacggtcgt caaaagaaa    2520
ctatccgaga tccaactgga taaaacaggt catttcccaa tgtacgggaa agaaagcgat    2580
ccaaggacat atgaagccat cgccaacgg ttgcttgaac ataacaatga cccaaaaaag    2640
gcgtttcaag agcctctgta taaaccgaag aagaacggag aactaggtcc tatcatccga    2700
acaatcaaaa tcatcgatac gacaaatcaa gttattccgc tcaacgatgg caaaacagtc    2760
gcctacaaca gcaacatcgt gcgggtcgac gtctttgaga agatggcaa atattattgt    2820
gtccctatct atacaataga tatgatgaaa gggatcttgc caaacaaggc gatcgagccg    2880
aacaaaccgt actctgagtg gaaggaaatg acggaggact atacattccg attcagtcta    2940
tacccaaatg atcttatccg tatcgaattt ccccgagaaa aaacaataaa gactgctgtg    3000
ggggaagaaa tcaaaattaa ggatctgttc gcctattatc aaaccatcga ctcctccaat    3060
ggagggttaa gtttggttag ccatgataac aactttttcgc tccgcagcat cggttcaaga    3120
accctcaaac gattcgagaa ataccaagta gatgtgctag caacatcta caaagtgaga    3180
ggggaaaaga gagttggggt ggcgtcatct tctcattcga aagccgggga aactatccgt    3240
ccgttataa                                                           3249
```

<210> SEQ ID NO 8
<211> LENGTH: 1045
<212> TYPE: PRT
<213> ORGANISM: Actinomyces naeslundii

<400> SEQUENCE: 8

Met Trp Tyr Ala Ser Leu Met Ser Ala His His Leu Arg Val Gly Ile
1               5                   10                  15

Asp Val Gly Thr His Ser Val Gly Leu Ala Thr Leu Arg Val Asp Asp
            20                  25                  30

His Gly Thr Pro Ile Glu Leu Leu Ser Ala Leu Ser His Ile His Asp
        35                  40                  45

Ser Gly Val Gly Lys Glu Gly Lys Lys Asp His Asp Thr Arg Lys Lys
    50                  55                  60

Leu Ser Gly Ile Ala Arg Arg Ala Arg Arg Leu Leu His His Arg Arg

```
                65                  70                  75                  80
Thr Gln Leu Gln Gln Leu Asp Glu Val Leu Arg Asp Leu Gly Phe Pro
                    85                  90                  95
Ile Pro Thr Pro Gly Glu Phe Leu Asp Leu Asn Glu Gln Thr Asp Pro
                100                 105                 110
Tyr Arg Val Trp Arg Val Arg Ala Arg Leu Val Glu Lys Leu Pro
                115                 120                 125
Glu Glu Leu Arg Gly Pro Ala Ile Ser Met Ala Val Arg His Ile Ala
            130                 135                 140
Arg His Arg Gly Trp Arg Asn Pro Tyr Ser Lys Val Glu Ser Leu Leu
145                 150                 155                 160
Ser Pro Ala Asn Ala Asn Glu Ile Arg Lys Ile Cys Ala Arg Gln Gly
                    165                 170                 175
Val Ser Pro Asp Val Cys Lys Gln Leu Leu Arg Ala Val Phe Lys Ala
                180                 185                 190
Asp Ser Pro Arg Gly Ser Ala Val Ser Arg Val Ala Pro Asp Pro Leu
                195                 200                 205
Pro Gly Gln Gly Ser Phe Arg Arg Ala Pro Lys Cys Asp Pro Glu Phe
            210                 215                 220
Gln Arg Phe Arg Ile Ile Ser Ile Val Ala Asn Leu Arg Ile Ser Glu
225                 230                 235                 240
Thr Lys Gly Glu Asn Arg Pro Leu Thr Ala Asp Glu Arg Arg His Val
                    245                 250                 255
Val Thr Phe Leu Thr Glu Asp Ser Gln Ala Asp Leu Thr Trp Val Asp
                260                 265                 270
Val Ala Glu Lys Leu Gly Val His Arg Arg Asp Leu Arg Gly Thr Ala
            275                 280                 285
Val His Thr Asp Asp Gly Glu Arg Ser Ala Ala Arg Pro Pro Ile Asp
            290                 295                 300
Ala Thr Asp Arg Ile Met Arg Gln Thr Lys Ile Ser Ser Leu Lys Thr
305                 310                 315                 320
Trp Trp Glu Glu Ala Asp Ser Glu Gln Arg Gly Ala Met Ile Arg Tyr
                    325                 330                 335
Leu Tyr Glu Asp Pro Thr Asp Ser Glu Cys Ala Glu Ile Ile Ala Glu
                340                 345                 350
Leu Pro Glu Glu Asp Gln Ala Lys Leu Asp Ser Leu His Leu Pro Ala
            355                 360                 365
Gly Arg Ala Ala Tyr Ser Arg Glu Ser Leu Thr Ala Leu Ser Asp His
            370                 375                 380
Met Leu Ala Thr Thr Asp Asp Leu His Glu Ala Arg Lys Arg Leu Phe
385                 390                 395                 400
Gly Val Asp Asp Ser Trp Ala Pro Pro Ala Glu Ala Ile Asn Ala Pro
                    405                 410                 415
Val Gly Asn Pro Ser Val Asp Arg Thr Leu Lys Ile Val Gly Arg Tyr
                420                 425                 430
Leu Ser Ala Val Glu Ser Met Trp Gly Thr Pro Glu Val Ile His Val
            435                 440                 445
Glu His Val Arg Asp Gly Phe Thr Ser Glu Arg Met Ala Asp Glu Arg
            450                 455                 460
Asp Lys Ala Asn Arg Arg Arg Tyr Asn Asp Asn Gln Glu Ala Met Lys
465                 470                 475                 480
Lys Ile Gln Arg Asp Tyr Gly Lys Glu Gly Tyr Ile Ser Arg Gly Asp
                    485                 490                 495
```

```
Ile Val Arg Leu Asp Ala Leu Glu Leu Gln Gly Cys Ala Cys Leu Tyr
            500                 505                 510
Cys Gly Thr Thr Ile Gly Tyr His Thr Cys Gln Leu Asp His Ile Val
        515                 520                 525
Pro Gln Ala Gly Pro Gly Ser Asn Asn Arg Arg Gly Asn Leu Val Ala
    530                 535                 540
Val Cys Glu Arg Cys Asn Arg Ser Lys Ser Asn Thr Pro Phe Ala Val
545                 550                 555                 560
Trp Ala Gln Lys Cys Gly Ile Pro His Val Gly Val Lys Glu Ala Ile
            565                 570                 575
Gly Arg Val Arg Gly Trp Arg Lys Gln Thr Pro Asn Thr Ser Ser Glu
        580                 585                 590
Asp Leu Thr Arg Leu Lys Lys Glu Val Ile Ala Arg Leu Arg Arg Thr
    595                 600                 605
Gln Glu Asp Pro Glu Ile Asp Glu Arg Ser Met Glu Ser Val Ala Trp
610                 615                 620
Met Ala Asn Glu Leu His His Arg Ile Ala Ala Ala Tyr Pro Glu Thr
625                 630                 635                 640
Thr Val Met Val Tyr Arg Gly Ser Ile Thr Ala Ala Arg Lys Ala
            645                 650                 655
Ala Gly Ile Asp Ser Arg Ile Asn Leu Ile Gly Glu Lys Gly Arg Lys
        660                 665                 670
Asp Arg Ile Asp Arg Arg His His Ala Val Asp Ala Ser Val Val Ala
    675                 680                 685
Leu Met Glu Ala Ser Val Ala Lys Thr Leu Ala Glu Arg Ser Ser Leu
    690                 695                 700
Arg Gly Glu Gln Arg Leu Thr Gly Lys Glu Gln Thr Trp Lys Gln Tyr
705                 710                 715                 720
Thr Gly Ser Thr Val Gly Ala Arg Glu His Phe Glu Met Trp Arg Gly
            725                 730                 735
His Met Leu His Leu Thr Glu Leu Phe Asn Glu Arg Leu Ala Glu Asp
        740                 745                 750
Lys Val Tyr Val Thr Gln Asn Ile Arg Leu Arg Leu Ser Asp Gly Asn
    755                 760                 765
Ala His Thr Val Asn Pro Ser Lys Leu Val Ser His Arg Leu Gly Asp
    770                 775                 780
Gly Leu Thr Val Gln Gln Ile Asp Arg Ala Cys Thr Pro Ala Leu Trp
785                 790                 795                 800
Cys Ala Leu Thr Arg Glu Lys Asp Phe Asp Lys Asn Gly Leu Pro
            805                 810                 815
Ala Arg Glu Asp Arg Ala Ile Arg Val His Gly His Glu Ile Lys Ser
        820                 825                 830
Ser Asp Tyr Ile Gln Val Phe Ser Lys Arg Lys Thr Asp Ser Asp
    835                 840                 845
Arg Asp Glu Thr Pro Phe Gly Ala Ile Ala Val Arg Gly Gly Phe Val
    850                 855                 860
Glu Ile Gly Pro Ser Ile His His Ala Arg Ile Tyr Arg Val Glu Gly
865                 870                 875                 880
Lys Lys Pro Val Tyr Ala Met Leu Arg Val Phe Thr His Asp Leu Leu
            885                 890                 895
Ser Gln Arg His Gly Asp Leu Phe Ser Ala Val Ile Pro Pro Gln Ser
        900                 905                 910
```

```
Ile Ser Met Arg Cys Ala Glu Pro Lys Leu Arg Lys Ala Ile Thr Thr
        915                 920                 925

Gly Asn Ala Thr Tyr Leu Gly Trp Val Val Gly Asp Glu Leu Glu
        930                 935                 940

Ile Asn Val Asp Ser Phe Thr Lys Tyr Ala Ile Gly Arg Phe Leu Glu
945                 950                 955                 960

Asp Phe Pro Asn Thr Thr Arg Trp Arg Ile Cys Gly Tyr Asp Thr Asn
                965                 970                 975

Ser Lys Leu Thr Leu Lys Pro Ile Val Leu Ala Ala Glu Gly Leu Glu
                980                 985                 990

Asn Pro Ser Ser Ala Val Asn Glu Ile Val Glu Leu Lys Gly Trp Arg
                995                 1000                1005

Val Ala Ile Asn Val Leu Thr Lys Val His Pro Thr Val Val Arg
        1010                1015                1020

Arg Asp Ala Leu Gly Arg Pro Arg Tyr Ser Ser Arg Ser Asn Leu
        1025                1030                1035

Pro Thr Ser Trp Thr Ile Glu
        1040                1045

<210> SEQ ID NO 9
<211> LENGTH: 1160
<212> TYPE: PRT
<213> ORGANISM: Streptococcus pyogenes

<400> SEQUENCE: 9

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Arg
            180                 185                 190

Lys Gln Arg Thr Phe Asp Asn Gly Ser Ile Pro His Gln Ile His Leu
        195                 200                 205

Gly Glu Leu His Ala Ile Leu Arg Arg Gln Glu Asp Phe Tyr Pro Phe
    210                 215                 220

Leu Lys Asp Asn Arg Glu Lys Ile Glu Lys Ile Leu Thr Phe Arg Ile
225                 230                 235                 240
```

```
Pro Tyr Tyr Val Gly Pro Leu Ala Arg Gly Asn Ser Arg Phe Ala Trp
                245                 250                 255

Met Thr Arg Lys Ser Glu Glu Thr Ile Thr Pro Trp Asn Phe Glu Glu
                260                 265                 270

Val Val Asp Lys Gly Ala Ser Ala Gln Ser Phe Ile Glu Arg Met Thr
                275                 280                 285

Asn Phe Asp Lys Asn Leu Pro Asn Glu Lys Val Leu Pro Lys His Ser
            290                 295                 300

Leu Leu Tyr Glu Tyr Phe Thr Val Tyr Asn Glu Leu Thr Lys Val Lys
305                 310                 315                 320

Tyr Val Thr Glu Gly Met Arg Lys Pro Ala Phe Leu Ser Gly Glu Gln
                325                 330                 335

Lys Lys Ala Ile Val Asp Leu Leu Phe Lys Thr Asn Arg Lys Val Thr
                340                 345                 350

Val Lys Gln Leu Lys Glu Asp Tyr Phe Lys Lys Ile Glu Cys Phe Asp
                355                 360                 365

Ser Val Glu Ile Ser Gly Val Glu Asp Arg Phe Asn Ala Ser Leu Gly
            370                 375                 380

Thr Tyr His Asp Leu Leu Lys Ile Ile Lys Asp Lys Asp Phe Leu Asp
385                 390                 395                 400

Asn Glu Glu Asn Glu Asp Ile Leu Glu Asp Ile Val Leu Thr Leu Thr
                405                 410                 415

Leu Phe Glu Asp Arg Glu Met Ile Glu Glu Arg Leu Lys Thr Tyr Ala
                420                 425                 430

His Leu Phe Asp Asp Lys Val Met Lys Gln Leu Lys Arg Arg Arg Tyr
                435                 440                 445

Thr Gly Trp Gly Arg Leu Ser Arg Lys Leu Ile Asn Gly Ile Arg Asp
450                 455                 460

Lys Gln Ser Gly Lys Thr Ile Leu Asp Phe Leu Lys Ser Asp Gly Phe
465                 470                 475                 480

Ala Asn Arg Asn Phe Met Gln Leu Ile His Asp Asp Ser Leu Thr Phe
                485                 490                 495

Lys Glu Asp Ile Gln Lys Ala Gln Val Ser Gly Gln Gly Asp Ser Leu
                500                 505                 510

His Glu His Ile Ala Asn Leu Ala Gly Ser Pro Ala Ile Lys Lys Gly
                515                 520                 525

Ile Leu Gln Thr Val Lys Val Val Asp Glu Leu Val Lys Val Met Gly
            530                 535                 540

Arg His Lys Pro Glu Asn Ile Val Ile Glu Met Ala Arg Glu Asn Gln
545                 550                 555                 560

Thr Thr Gln Lys Gly Gln Lys Asn Ser Arg Glu Arg Met Lys Arg Ile
                565                 570                 575

Glu Glu Gly Ile Lys Glu Leu Gly Ser Gln Ile Leu Lys Glu His Pro
                580                 585                 590

Val Glu Asn Thr Gln Leu Gln Asn Glu Lys Leu Tyr Leu Tyr Tyr Leu
                595                 600                 605

Gln Asn Gly Arg Asp Met Tyr Val Asp Gln Glu Leu Asp Ile Asn Arg
            610                 615                 620

Leu Ser Asp Tyr Asp Val Asp His Ile Val Pro Gln Ser Phe Leu Lys
625                 630                 635                 640

Asp Asp Ser Ile Asp Asn Lys Val Leu Thr Arg Ser Asp Lys Asn Arg
                645                 650                 655
```

```
Gly Lys Ser Asp Asn Val Pro Ser Glu Val Val Lys Met Lys
            660             665             670

Asn Tyr Trp Arg Gln Leu Leu Asn Ala Lys Leu Ile Thr Gln Arg Lys
            675             680             685

Phe Asp Asn Leu Thr Lys Ala Glu Arg Gly Gly Leu Ser Glu Leu Asp
            690             695             700

Lys Ala Gly Phe Ile Lys Arg Gln Leu Val Glu Thr Arg Gln Ile Thr
705             710             715             720

Lys His Val Ala Gln Ile Leu Asp Ser Arg Met Asn Thr Lys Tyr Asp
                725             730             735

Glu Asn Asp Lys Leu Ile Arg Glu Val Lys Val Ile Thr Leu Lys Ser
            740             745             750

Lys Leu Val Ser Asp Phe Arg Lys Asp Phe Gln Phe Tyr Lys Val Arg
755             760             765

Glu Ile Asn Asn Tyr His His Ala His Asp Ala Tyr Leu Asn Ala Val
            770             775             780

Val Gly Thr Ala Leu Ile Lys Lys Tyr Pro Lys Leu Glu Ser Glu Phe
785             790             795             800

Val Tyr Gly Asp Tyr Lys Val Tyr Asp Val Arg Lys Met Ile Ala Lys
                805             810             815

Ser Glu Gln Glu Ile Gly Lys Ala Thr Ala Lys Tyr Phe Phe Tyr Ser
            820             825             830

Asn Ile Met Asn Phe Phe Lys Thr Glu Ile Thr Leu Ala Asn Gly Glu
            835             840             845

Ile Arg Lys Arg Pro Leu Ile Glu Thr Asn Gly Glu Thr Gly Glu Ile
850             855             860

Val Trp Asp Lys Gly Arg Asp Phe Ala Thr Val Arg Lys Val Leu Ser
865             870             875             880

Met Pro Gln Val Asn Ile Val Lys Lys Thr Glu Val Gln Thr Gly Gly
                885             890             895

Phe Ser Lys Glu Ser Ile Leu Pro Lys Arg Asn Ser Asp Lys Leu Ile
            900             905             910

Ala Arg Lys Lys Asp Trp Asp Pro Lys Lys Tyr Gly Gly Phe Asp Ser
            915             920             925

Pro Thr Val Ala Tyr Ser Val Leu Val Val Ala Lys Val Glu Lys Gly
930             935             940

Lys Ser Lys Lys Leu Lys Ser Val Lys Glu Leu Leu Gly Ile Thr Ile
945             950             955             960

Met Glu Arg Ser Ser Phe Glu Lys Asn Pro Ile Asp Phe Leu Glu Ala
                965             970             975

Lys Gly Tyr Lys Glu Val Lys Lys Asp Leu Ile Ile Lys Leu Pro Lys
            980             985             990

Tyr Ser Leu Phe Glu Leu Glu Asn Gly Arg Lys Arg Met Leu Ala Ser
            995             1000             1005

Ala Gly Glu Leu Gln Lys Gly Asn Glu Leu Ala Leu Pro Ser Lys
        1010             1015             1020

Tyr Val Asn Phe Leu Tyr Leu Ala Ser His Tyr Glu Lys Leu Lys
        1025             1030             1035

Gly Ser Pro Glu Asp Asn Glu Gln Lys Gln Leu Phe Val Glu Gln
        1040             1045             1050

His Lys His Tyr Leu Asp Glu Ile Ile Glu Gln Ile Ser Glu Phe
        1055             1060             1065

Ser Lys Arg Val Ile Leu Ala Asp Ala Asn Leu Asp Lys Val Leu
```

-continued

```
           1070                1075                1080
Ser Ala Tyr Asn Lys His Arg Asp Lys Pro Ile Arg Glu Gln Ala
       1085                1090                1095

Glu Asn Ile Ile His Leu Phe Thr Leu Thr Asn Leu Gly Ala Pro
       1100                1105                1110

Ala Ala Phe Lys Tyr Phe Asp Thr Thr Ile Asp Arg Lys Arg Tyr
       1115                1120                1125

Thr Ser Thr Lys Glu Val Leu Asp Ala Thr Leu Ile His Gln Ser
       1130                1135                1140

Ile Thr Gly Leu Tyr Glu Thr Arg Ile Asp Leu Ser Gln Leu Gly
       1145                1150                1155

Gly Asp
    1160
```

THERMOSTABLE CAS9 NUCLEASES

CROSS-REFERENCE TO RELATED APPLICATIONS

This application is a continuation of U.S. patent application Ser. No. 15/735,359 filed Dec. 11, 2017, which is a U.S. national phase application filed under 35 U.S.C. § 371 claiming benefit to International Patent Application No. PCT/EP2016/062817, filed on Jun. 6, 2016, which claims priority to Great Britain provisional application no. 1510296.5, filed Jun. 12, 2015, the disclosures of which are incorporated herein by reference in their entirety.

FIELD OF THE INVENTION

The present invention relates to the field of genetic engineering and more particularly to nucleic acid editing and genome modification. The present invention concerns genetic engineering tools in the form of nucleases which can be configured for sequence-directed site-specific nicking or cutting of genetic material; also ribonucleoproteins which exert nuclease activity on sequence specific sites of genetic material, and modified nucleases and ribonucleoproteins for use as markers. The invention therefore also concerns associated expression constructs for delivery and expression of nucleases and guide RNAs within cells. Further, the invention concerns the sequence-specific editing of nucleic acids in vitro or in vivo and methods used to achieve that. A particular area to which the invention relates is the genetic manipulation of thermophilic organisms, particularly microorganisms.

BACKGROUND TO THE INVENTION

It was first demonstrated in 2007 that CRISPR-Cas is an adaptive immune system in many bacteria and most archaea (Barrangou et al., 2007, Science 315: 1709-1712), Brouns et al., 2008, Science 321: 960-964). Based on functional and structural criteria, three types of CRISPR-Cas systems have so far been characterized, most of which use small RNA molecules as guide to target complementary DNA sequences (Makarova et al., 2011, Nat Rev Microbiol 9: 467-477; Van der Oost et al., 2014, Nat Rev Microbiol 12: 479-492).

In a recent study by the Doudna/Charpentier labs, a thorough characterization of the effector enzyme of the type II CRISPR-Cas system (Cas9) was performed, including demonstration that the introduction of designed CRISPR RNA guides (with specific spacer sequences) targets complementary sequences (protospacers) on a plasmid, causing double strand breaks of this plasmid (Jinek et al., 2012, Science 337: 816-821). Following Jinek et al., 2012, Cas9 is used as a tool for genome editing.

Cas9 has been used to engineer the genomes of a range of eukaryotic cells (e.g. fish, plant, man) (Charpentier and Doudna, 2013, Nature 495: 50-51).

In addition, Cas9 has been used to improve yields of homologous recombination in bacteria by selecting for dedicated recombination events (Jiang et al., 2013, Nature Biotechnol 31: 233-239). To achieve this, a toxic fragment (Targeting construct) is co-transfected with a rescuing fragment carrying the desired alteration (Editing construct, carrying point mutation or deletions). The Targeting construct consists of Cas9 in combination with a design CRISPR and an antibiotic resistance marker, defining the site of the desired recombination on the host chromosome; in the presence of the corresponding antibiotic, integration of the Targeting construct in the host chromosome is selected for. Only when the additional recombination occurs of the Editing construct with the CRISPR target site elsewhere on the host chromosome, the host can escape from the auto-immunity problem. Hence, in the presence of the antibiotic, only the desired (marker-free) mutants are able to survive and grow. A related strategy to select for subsequent removal of the integrated Targeting construct from the chromosome is presented as well, generating a genuine marker free mutant.

It has been established in recent years that CRISPR-Cas mediated genome editing constitutes a useful tool for genetic engineering. It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10:957-963, for example), requiring only modification of the guide sequence in order to target sequences of interest.

However, there is a continuing need for the development of agents with improved sequence-specific nucleic acid detection, cleavage and manipulation under a variety of experimental conditions for application in the area of genetic research and genome editing. In particular, currently available sequence-specific genome editing tools, including Cas9, are not applicable for use in all conditions or organisms, for example, sequence-specific nucleases are relatively thermo-sensitive and therefore not applicable for use in strictly thermophilic microorganisms (which are capable of growth between 41° C. and 122° C. and grow optimally in the ranges of temperatures from >60° C. to 80° C. with hyperthermophiles capable of optimal growth above 80° C.), for example, microorganisms that are used in industrial fermentations or for in vitro laboratory processes conducted at elevated temperatures.

To date there is no experimental evidence for active Cas9 proteins in thermophiles. Based on a comparative genome screening by Chylinski et al. (2014; Nucleic Acids Research 42: 6091-61-05) on the presence of Cas9 in bacteria it was found that the Type II-C CRISPR-Cas system is only present in approximately 3.3% of all bacterial genomes. Among thermophilic bacteria, the Type II system is underrepresented based on statistical analysis (P=0.0019). In addition, no Type II system has been found in archaea however, this could possibly be due to the absence of the RNase III protein (involved in the Type II system) in archaea. Chylinski, et al., (2014; Nucleic Acids Research 42: 6091-6105) did describe the classification and evolution of type II CRISPR-Cas systems, in particular, two species are identified which exhibit these systems, however these species grow maximally at 55° C. and do not exhibit strictly thermophilic growth with optimum growth temperature 60-80° C., with hyperthermophiles capable of growing optimally above 80° C.

Despite the rarity of the CRISPR-Cas system in bacterial genomes and in particular the fact that Cas9 has been found only in bacteria (not archaea) with optimal growth temperatures below 45° C., the inventors have surprisingly discovered several thermostable Cas9 variants which enable genome editing to be carried out at elevated temperatures. These Cas9 nucleases provide novel tools for genetic engineering at elevated temperatures and are of particular value in the genetic manipulation of thermophilic organisms; particularly microorganisms.

SUMMARY OF THE INVENTION

Accordingly, the present invention provides an isolated clustered regularly interspaced short palindromic repeat (CRISPR)-associated (Cas) protein or polypeptide comprising;

a. the amino acid motif EKDGKYYC [SEQ ID NO: 2]; and/or
b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
d. the amino acid motif $X_7VYSX_3K$ [SEQ ID NO: 5] wherein $X_7$ is Glutamate or Isoleucine and $X_8$ is one of Tryptophan, Serine or Lysine; and/or
e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

A polypeptide in the context of this invention may be viewed as a fragment of the full length Cas protein. Such fragments may be inactive and used in ways and for purposes not associated directly with editing or cutting of genetic material, for example for standards in assays or raising antibodies or the like.

In preferred embodiments however, the Cas protein or polypeptide is functional and capable of DNA cleavage at a temperature in the range 50° C. and 100° C., inclusive, when associated with at least one targeting RNA molecule, and a polynucleotide comprising a target nucleic acid sequence recognised by the targeting RNA molecule.

In particular embodiments, the invention may provide a Cas protein or polypeptide comprising the amino acid motif EKDGKYYC [SEQ ID NO: 2]. In other embodiments, the Cas proteins or polypeptides may further comprise the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

In other embodiments the Cas proteins or polypeptides defined herein may additionally further comprise the amino acid motif $X_5LKX_6IE$ [SEQ ID NO: 4] wherein $X_5$ is independently selected from Methionine or Phenylalanine and $X_6$ is independently selected from Histidine or Asparagine.

In other embodiments, the Cas proteins or polypeptides defined herein may additionally further comprise the amino acid motif $X_7VYSX_8K$ [SEQ ID NO: 5] wherein $X_7$ is Glutamate or Isoleucine and $X_8$ is one of Tryptophan, Serine or Lysine.

In other embodiments, the Cas proteins or polypeptides defined herein may additionally further comprise the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In accordance with the present invention, it may be appreciated that a Cas protein or polypeptide of the invention may comprise any of the motifs of SEQ ID NOs 2 to 6, either alone or in combination. The following summarises each of the combinations of motifs which may characterize Cas proteins or polypeptides of the invention:

[SEQ ID NO: 2]
EKDGKYYC.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_1$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_7VYSX_8K$ [SEQ ID NO: 5] wherein $X_7$ is Glutamate or Isoleucine and $X_9$ is one of Tryptophan, Serine or Lysine;

and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In another aspect, the present invention provides an isolated Cas protein or polypeptide fragment thereof having an amino acid sequence of SEQ ID NO: 1 or a sequence of at least 77% identity therewith, wherein the Cas protein or polypeptide is capable of DNA cleavage at a temperature in the range 50° C. and 100° C. inclusive.

Preferably, the Cas protein or polypeptide is capable of DNA cleavage at a temperature in the range 60° C. to 80° C. inclusive. For example, the DNA cleavage occurs at a temperature of 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C. More preferably the Cas protein or polypeptide is capable of DNA cleavage at a temperature in the range 60 to 65° C. In preferred aspects, a Cas protein or polypeptide fragment of the invention may comprises an amino acid sequence of at least 75% identity; preferably at least 85%; more preferably at least 90%; even more preferably at least 95% identity to SEQ ID NO: 1.

More particularly, a Cas protein or polypeptide of the invention may comprise an amino acid sequence with a percentage identity with SEQ ID NO:1 as follows: at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.8%.

The percentage amino acid sequence identity with SEQ ID NO: 1 is determinable as a function of the number of identical positions shared by the sequences in a selected comparison window, taking into account the number of gaps, and the length of each gap, which need to be introduced for optimal alignment of the two sequences.

A Cas protein or polypeptide fragment of the invention may be characterised in terms of both the reference sequence SEQ ID NO: 1 and any aforementioned percentage variant thereof as defined by percentage sequence identity, alone or in combination with any of the aforementioned amino acid motifs (i.e. SEQ ID NOS 2 and/or 3 and/or 4 and/or 5 and/or 6) as essential features.

Also, the invention provides nucleic acids encoding any of the aforementioned proteins or polypeptides of the invention. The nucleic acids may be isolated or in the form of expression constructs.

In all aforementioned aspects of the present invention, amino acid residues may be substituted conservatively or non-conservatively. Conservative amino acid substitutions refer to those where amino acid residues are substituted for other amino acid residues with similar chemical properties (e.g., charge or hydrophobicity) and therefore do not alter the functional properties of the resulting polypeptide.

Similarly it will be appreciated by a person of average skill in the art that nucleic acid sequences may be substituted conservatively or non-conservatively without affecting the function of the polypeptide. Conservatively modified nucleic acids are those substituted for nucleic acids which encode identical or functionally identical variants of the amino acid sequences. It will be appreciated by the skilled reader that each codon in a nucleic acid (except AUG and UGG; typically the only codons for methionine or tryptophan, respectively) can be modified to yield a functionally identical molecule. Accordingly, each silent variation (i.e. synonymous codon) of a polynucleotide or polypeptide, which encodes a polypeptide of the present invention, is implicit in each described polypeptide sequence.

Cleavage Temperatures

The temperature range, including optimal temperature range of nuclease activity of the Cas proteins of the present invention is significantly higher than that of known Cas9 proteins. Also, the upper extent of the range in which it retains nuclease activity is much higher than that of known Cas9 proteins. A higher optimal temperature and functional range provides a significant advantage in genetic engineering at high temperatures and therefore, for example, in the editing the genomes of thermophilic organisms, many of which have utility in a range of industrial, agricultural and pharmaceutical processes conducted at elevated temperatures.

Advantageously, Cas proteins or polypeptides of the invention are capable of nucleic acid cleavage from 20° C. to 100° C. but are particularly useful at elevated temperatures, for example between 41° C. and 122° C., preferably between 50° C. and 100° C. Cas proteins and polypeptides of the invention are capable of cleaving DNA, RNA and synthetic nucleic acids. Cas proteins or polypeptides of the invention are may also provide operability for nuclease activity and gene editing applications at temperatures in the range 20 to 40° C., for example.

Preferably, Cas proteins or polypeptides of the invention, when associated with suitable gRNA (guide RNA) which recognizes a target sequence in the polynucleotide molecule(s) to be cleaved, marked or modified, does so at temperatures in the range 50° C. to 100° C., optionally in the range 55° C. to 100° C., 60° C. to 100° C., 65° C. to 100° C., 70° C. to 100° C., 75° C. to 100° C., 80° C. to 100° C., 85° C. to 100° C., 90° C. to 100° C., 95° C. to 100° C. More preferably, Cas proteins of the invention cleave, mark or modify nucleic acids at temperatures in the range 51° C. to 99° C., 52° C. to 98° C., 53° C. to 97° C., 54° C. to 96° C., 55° C. to 95° C., 56° C. to 94° C., 57° C. to 93° C., 58° C. to 92° C., 59° C. to 91° C. 60° C. to 90° C., 61° C. to 89° C., 62° C. to 88° C., 63° C. to 87° C., 64° C. to 86° C., 65° C. to 85° C., 66° C. to 84° C., 67° C. to 83° C., 68° C. to 82° C., 69° C. to 81° C. 70° C. to 80° C., 71° C. to 79° C., 72° C. to 78° C., 73° C. to 77° C., 74° C. to 76° C., 75° C. Preferably, Cas proteins of the invention cleave, mark or modify nucleic acids at temperatures in the range 60° C. to 80° C., 61° C. to 79° C., 62° C. to 78° C., 63° C. to 77° C., 64° C. to 76° C., 60° C. to 75° C., 60° C. to 70° C. Optimally Cas proteins of the invention cleave, mark or modify nucleic acids at temperatures in the range 60° C. to 65° C., preferably at 65° C.

In all aspects of the invention, Cas proteins or polypeptides may be obtained or derived from bacteria, archaea or viruses; or alternatively may be synthesised de novo. In preferred embodiments, a Cas protein or polypeptide of the invention is derived from a thermophilic prokaryotic organism, which may be classified as an archaea or bacterium, but is preferably a bacterium. More preferably a Cas protein or polypeptide of the invention will be derived from a thermophilic bacterium. Herein, the term thermophilic is to be understood as meaning capable of survival and growth at relatively high temperatures, for example in the context of the invention, capable of nucleic acid cleavage between 41 and 122° C. (106 and 252° F.). Preferably a Cas protein or polypeptide of the invention may be isolated from one or more thermophilic bacteria and will function above 60° C. Preferably a Cas protein or polypeptide of the invention may be isolated from one or more thermophilic bacteria and will function in the range 60° C. to 80° C. and optimally between 60° C. and 65° C. In preferred embodiments, a Cas protein or polypeptide of the invention is derived from *Geobacillus* sp. More preferably, a Cas protein of the invention is derived from *Geobacillus thermodenitrificans*. Even more preferably, a Cas protein of the invention is derived from *Geobacillus thermodenitrificans* T12. A Cas protein or polypeptide of the invention may be derived from a virus.

RNA Guides and Target Sequences

Cas proteins of the invention allow for sequence-specific cleavage, tagging, marking or modification of target nucleic acids at elevated temperatures. Target nucleic acids may be DNA (single-stranded or double-stranded), RNA or synthetic nucleic acids. A particularly useful application of the present invention is the sequence-specific targeting and modification of genomic DNA by one or more Cas proteins of the invention in complex with one or more guide RNAs (gRNAs) that complementarily bind to a targeted sequence of the genomic DNA. Consequently, the target nucleic acid is preferably double-stranded DNA. Such targeting may be performed in vitro or in vivo. Preferably such targeting is performed in vivo. In this way, Cas proteins of the invention may be used to target and modify specific DNA sequences located in the genomic DNA of a cell. It is envisaged that the Cas system may be used to modify genomes in a variety of cell types of and/or in different organisms.

Accordingly, the present invention provides a ribonucleoprotein complex comprising a Cas protein or a polypeptide of the invention as hereinbefore described, and further comprising at least one RNA molecule which has a targeting function in that it recognizes a particular nucleotide sequence in a target polynucleotide. Preferably, the RNA molecule is a single-stranded RNA molecule, e.g. a CRISPR RNA (crRNA) and is associated, e.g. by hybridization with a tracrRNA. The targeting RNA may be a chimera of a crRNA and tracrRNA. The aforementioned RNA molecules may have a ribonucleotide sequence of at least 90% identity, or complementarity to a target nucleotide sequence. Optionally, the RNA molecule has a ribonucleotide sequence of at least 90%, at least 91%, at least 92%, at least 93%, at least 94%, at least 95%, at least 96%, at least 97%, at least 98%, at least 99% or 100% identity or complementarity to a target nucleotide sequence. The preferred target nucleotide sequence is a DNA.

In a preferred aspect, the present invention provides a ribonucleoprotein complex as hereinbefore described, wherein the at least one targeting RNA molecule is substantially complementary along its length to a target DNA sequence.

Alteration of the sequence of the RNA guide which associates with the Cas protein of the invention therefore allows the Cas protein to be programmed to mark or cut double-stranded DNA at sites complementary to the guide RNA.

Preferably, the length of the at least one targeting RNA molecule in a ribonucleoprotein complex of the invention is in the range 35 to 135 residues, optionally in the range 35 to 134 residues, 35 to 133 residues, 35 to 132 residues, 35 to 131 residues, 35 to 130 residues, 35 to 129 residues, 35 to 128 residues, 35 to 127 residues, 35 to 126 residues, 35 to 125 residues, 35 to 124 residues, 35 to 123 residues, 35 to 122 residues, 35 to 121 residues, 35 to 120 residues, 35 to 119 residues, 35 to 118 residues, 35 to 117 residues, 35 to 116 residues, 35 to 115 residues, 35 to 114 residues, 35 to 113 residues, 35 to 112 residues, 35 to 111 residues, 35 to 110 residues, 35 to 109 residues, 35 to 108 residues, 35 to 107 residues, 35 to 106 residues, 35 to 105 residues, 35 to 104 residues, 35 to 103 residues, 35 to 102 residues, 35 to 101 residues, 35 to 100 residues, 35 to 99 residues, 35 to 98 residues, 35 to 97 residues, 35 to 96 residues, 35 to 95 residues, to 94 residues, 35 to 93 residues, 35 to 92 residues, 35 to 91 residues, 35 to 90 residues, 35 to 89 residues, 35 to 88 residues, 35 to 87 residues, 35 to 86 residues, to 85 residues, 35 to 84 residues, 35 to 83 residues, 35 to 82 residues, 35 to 81 residues, 35 to 80 residues, 35 to 79 residues, 35 to 78 residues, 35 to 77 residues, to 76 residues, 35 to 75 residues, 35 to 74 residues, 35 to 73 residues, 35 to 72 residues, 35 to 71 residues, 35 to 70 residues, 35 to 69 residues, 35 to 68 residues, to 67 residues, 35 to 66 residues, 35 to 65 residues, 35 to 64 residues, 35 to 63 residues, 35 to 62 residues, 35 to 61 residues, 35 to 60 residues, 35 to 59 residues, to 58 residues, 35 to 57 residues, 35 to 56 residues, 35 to 55 residues, 35 to 54 residues, 35 to 53 residues, 35 to 52 residues, 35 to 51 residues, 35 to 50 residues, to 49 residues, 35 to 48 residues, 35 to 47 residues, 35 to 46 residues, 35 to 45 residues, 35 to 44 residues, 35 to 43 residues, 35 to 42 residues, 35 to 41 residues, to 40 residues, 35 to 39 residues, 35 to 38 residues, 35 to 37 residues, 35 to 36 residues or 35 residues. Preferably, the length of the at least one RNA molecule is in the range 36 to 174 residues, 37 to 173 residues, 38 to 172 residues, 39 to 171 residues, 40 to 170 residues, 41 to 169 residues, 42 to 168 residues, 43 to 167 residues, 44 to 166 residues, 45 to 165 residues, 46 to 164 residues, 47 to 163 residues, 48 to 162 residues, 49 to 161 residues, 50 to 160 residues, 51 to 159 residues, 52 to 158 residues, 53 to 157 residues, 54 to 156 residues, 36 to 74 residues, 37 to 73 residues, 38 to 72 residues, 39 to 71 residues, 40 to 70 residues, 41 to 69 residues, 42 to 68 residues, 43 to 67 residues, 44 to 66 residues, 45 to 65 residues, 46 to 64 residues, 47 to 63 residues, 48 to 62 residues, 49 to 61 residues, 50 to 60 residues, 51 to 59 residues, 52 to 58 residues, 53 to 57 residues, 54 to 56 residues.

In preferred aspects, the present invention provides a ribonucleoprotein complex, wherein the complementary portion of the at least one RNA molecule is at least 30 residues long. Alternatively, the complementary portion of the at least one RNA molecule may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 residues long.

The targeting RNA molecule will preferably require a high specificity and affinity for the target nucleic acid sequence. A dissociation constant ($K_d$) in the range 1 μM to 1 pM, preferably 1 nM to 1 pM; more preferably 1-100 pM is desirable as may be determined by native gel electrophoresis, or alternatively isothermal titration calorimetry, surface plasmon resonance, or fluorescence based titration methods. Affinity may be determined using an electrophoretic mobility shift assay (EMSA), also called gel retardation assay (see Semenova E et al. (2011) PNAS 108: 10098-10103).

The targeting RNA molecule is preferably modeled on what are known from nature in prokaryotes as CRISPR RNA (crRNA) molecules. The structure of crRNA molecules is already established and explained in more detail in Jore et al., 2011, Nature Structural & Molecular Biology 18: 529-537. In brief, a mature crRNA of type I-E is often 61 nucleotides long and consists of a 5' "handle" region of 8 nucleotides, the "spacer" sequence of 32 nucleotides, and a 3' sequence of 21 nucleotides which form a hairpin with a tetranucleotide loop (FIG. 5). Type I systems differ from type II (Cas9) and details of different systems are described in Van der Oost 2014 Nat Rev Micr 12: 479-492. In type II (Cas9) systems there is a different processing mechanism, making use of a second RNA (tracrRNA) and two ribonucleases. Rather than a hairpin, the mature crRNA in type II remains attached to a fragment of the tracrRNA (FIG. 5). However, the RNA used in the invention does not have to be designed strictly to the design of naturally occurring crRNA, whether in length, regions or specific RNA sequences. What is clear though, is that RNA molecules for use in the invention may be designed based on gene sequence information in the public databases or newly discovered, and then made artificially, e.g. by chemical synthesis in whole or in part. The RNA molecules of the invention may also be designed and produced by way of expression in genetically modified cells or cell free expression systems and this option may include synthesis of some or all of the RNA sequence.

The structure and requirements of crRNA in type II (Cas9) has also been described in Jinek et al., 2012 ibid. In type I, there is a so-called "SEED" portion forming the 5' end of the spacer sequence and which is flanked 5' thereto by the 5' handle of 8 nucleotides. Semenova et al. (2011, PNAS 108: 10098-10103), have found that all residues of the SEED sequence should be complementary to the target sequence, although for the residue at position 6, a mismatch may be tolerated (FIG. 5). In type II, there is a SEED of 10-12 nucleotides that is located at the 3' end of the spacer (FIG. 5) (reviewed by Van der Oost 2014 ibid.). Similarly, when designing and making an RNA component of a ribonucleoprotein complex of the invention directed at a target locus (i.e. sequence), the necessary match and mismatch rules for the type II SEED sequence can be applied.

The invention therefore includes a method of detecting and/or locating a single base change in a target nucleic acid molecule comprising contacting a nucleic acid sample with a ribonucleoprotein complex of the invention as hereinbefore described, or with a Cas protein or polypeptide and separate targeting RNA component of the invention as hereinbefore described, and wherein the sequence of the targeting RNA (including when in the ribonucleoprotein complex) is such that it discriminates between a normal allele and a mutant allele by virtue of a single base change at, for example, position 6 of a contiguous sequence of 8 nucleotide residues.

Without wishing to be bound by a particular theory, a design rule which may be used in preparing a targeting RNA component of ribonucleoprotein complexes of the invention involves the so-called "PAM" (protospacer adjacent motif) sequence in the target polynucleotide strand. The PAM sequence may be a conserved triplet of nucleotide residues, in the type I-E system of *E. coli* 5'-CTT-3', 5'-CAT-3', 5'-CCT-3', 5'-CAC-3', 5'-TTT-3', 5'-ATT-3', and 5'-AWG-3', wherein W is A, T or U. In Type I, a PAM sequence located in the targeted strand is usually at a position corresponding to 5' of the SEED. In Type II, however, the PAM is located at the other end, on the displaced strand close to the 3' end of the crRNA spacer, at a position corresponding to 3' of the seed (FIG. 5) (Jinek et al., 2012, op. cit.). For *Streptococcus pyogenes* Cas9, the PAM sequence has a conserved pair of nucleotide residues, 5'-NGG-3'. Recently, different Cas9 variants (Type IIA and Type IIC) (Ran et al., 2015 Nature 520:186-191)—FIG. 1A) have been characterized, and PAMs have been revealed (see Ran et al., 2015, ibid.—FIG. 1C). Currently established Cas9 PAMs include: Type IIA 5'-NGGNNNN-3' (*Streptococcus pyogenes*), 5'-NNGTNNN-3' (*Streptococcus pasteurianus*), 5'-NNGGAAN-3' (*Streptococcus thermophilus*), 5'-NNGGGNN-3' (*Staphylococcus aureus*), and Type IIC 5'-NGGNNNN-3' (*Corynebacterium difteriae*), 5'-NNGGGTN-3' (*Campylobacter lari*), 5'-NNNCATN-3' (*Parvobaculum lavamentivorans*), 5'-NNNNGTA-3' (*Neiseria cinerea*). Cas9 of *Geobacillus thermodenitrificans* T12 (this invention) belongs to Type IIC (Ran et al., 2015, ibid.). Therefore, although without wishing to be bound by a particular theory, the inventors expect that the PAM sequences more closely approximate those established for Type IIC Cas9 ribonucleoprotein complexes.

In embodiments of the invention, a targeting RNA molecule may have a length in the range of 35-75 residues. In preferred embodiments, the portion of the RNA which is complementary to and used for targeting a desired nucleic acid sequence is 31 or 32 residues long. In the context of a naturally-occurring crRNA, this would correspond to the spacer portion as shown for example in FIG. 1 of Semenova et al. (2011 ibid.).

A ribonucleoprotein complex of the invention may have a targeting component comprising 8 residues derived from the CRISPR repeat 5' to the RNA sequence which has substantial complementarity to the DNA target sequence. The RNA sequence having complementarity to the DNA target sequence would be understood to correspond in the context of a crRNA as being the spacer sequence. The 5' flanking sequence of the RNA would be considered to correspond to the 5' handle of a crRNA; as shown for example in FIG. 1 of Semenova et al. (2011 ibid.).

A ribonucleoprotein complex of the invention may have a hairpin and tetranucleotide loop forming sequence 3' to the targeting RNA sequence which has complementarity to a DNA target sequence, i.e. 3' to what would correspond to the 3' handle flanking the spacer sequence in a crRNA; for example as shown in FIG. 1 of Semenova et al. (2011 ibid.).

Without wishing to be bound by a particular theory, in a preferred ribonucleoprotein complex, the target sequence DNA strand which does not pair with the targeting RNA of the ribonucleoprotein complex may comprise a directly 3' adjacent triplet selected from 5'-NGGNNNN-3', 5'-NNGTNNN-3', 5'-NNGGAAN-3', 5'-NNGGGNN-3', 5'-NGGNNNN-3', 5'-NNGGGTN-3', 5'-NNNCATN-3', 5'-NNNNGTA-3' and wherein said triplet residues do not each pair with respective complementary DNA strand residues. However, it will be appreciated that other triplets or combinations of nucleotides may be used depending on the desired application. These triplets correspond to what is termed "protospacer adjacent motif" or "PAM" in the context of naturally occurring crRNAs. In type IIC CRISPR/Cas systems these PAM triplets are required for stable interaction with the Cascade/crRNA complex with its dsDNA target, in order to ensure high degree of specificity of the crRNA—both in the natural system targets and therefore preferably also of the RNAs according to the present invention—for the target sequence.

Functional Moieties

Advantageously, the ability of Cas proteins, polypeptides and riboucleoprotein complexes of the invention to target any polynucleotide sequence in a sequence-specific manner may be exploited in order to modify the target nucleic acid in some way, for example by cleaving it and/or marking it and/or modifying it. It will therefore be appreciated that additional proteins may be provided along with the Cas protein or polypeptide to achieve this. Accordingly, Cas proteins, polypeptides or ribonucleoprotein complexes of the present invention may be provided as part of a protein complex comprising at least one further protein. In a preferred aspect the present invention provides a Cas protein, polypeptide or a ribonucleoprotein complex wherein the Cas protein or at least one further protein further comprises at least one functional moiety. The at least one functional moiety may be fused or linked to the Cas protein. Preferably, the at least one functional moiety may be translationally fused to the Cas protein through expression in natural or artificial protein expression systems. Alternatively, the at least one functional moiety may be covalently linked by a chemical synthesis step to the Cas protein. Preferably, the at least one functional moiety is fused or linked to the N-terminus and/or the C-terminus of the Cas protein; preferably the N-terminus.

Desirably, the at least one functional moiety will be a protein. It may be a heterologous protein or alternatively may be native to the bacterial species from which the Cas protein was derived. The at least one functional moiety may be a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a particularly preferred aspect, the present invention provides a Cas protein, polypeptide, or a ribonucleoprotein complex, wherein the at least one functional moiety is a marker protein, for example GFP.

Nuclease Activity

A Cas ribonucleoprotein of any aspect of the invention has nucleic acid cleavage activity between 50° C. and 100° C. The ribonucleoproteins of the invention are capable of cleaving DNA, RNA or synthetic nucleic acids. In preferred aspects Cas ribonucleoproteins of the invention are capable of cleaving DNA in a sequence-specific manner, in particular double-stranded DNA.

In any aspect of the invention, Cas proteins, polypeptides or ribonucleoproteins of the invention may have more than one nuclease domain. Site-specific nucleases can permit the generation of double strand breaks (DSBs) at selected positions along a strand of DNA. In a target host cell, this enables DSBs to be made at specific pre-selected positions in the genome. The creation of such breaks by site-specific nucleases prompts the endogenous cellular repair machinery to be repurposed in order to insert, delete or modify DNA at desired positions in the genome of interest.

One or more nuclease activity sites of the protein or polypeptide molecule may be inactivated, e.g. so as to allow the activity of another functional moiety linked or fused to the protein or polypeptide, e.g. Fok1 nuclease.

Therefore notwithstanding the fact that the Cas proteins, polypeptides and ribonucleoproteins of the invention have endogenous nuclease activity, for certain applications it may be desirable to inactivate the native nuclease activity of the Cas protein and provide a Cas protein or a ribonucleoprotein complex wherein the native Cas9 nuclease activity is inactivated and the Cas protein is linked to at least one functional moiety. Reducing the incidence of mis-targeting events by complementation of the native Cas9 nuclease activity is one such application. This may desirably be achieved by inactivation of the native Cas9 nuclease activity of the Cas protein or ribonucleoprotein complex and provision of a heterologous nuclease, preferably fused to the Cas protein. Accordingly, the present invention provides a Cas protein or a ribonucleoprotein complex, wherein the at least one functional moiety is a nuclease domain, preferably a FokI nuclease domain. In a particularly preferred aspect, the Cas protein or ribonucleoprotein complex of the invention fused to a FokI nuclease domain is provided as part of a protein complex, preferably comprising another Cas protein or ribonucleoprotein complex of the invention fused to a FokI nuclease domain and wherein the two complexes target opposite strands of the target genomic DNA.

For some applications it may be desirable to completely attenuate the nuclease activity of the Cas protein, polypeptide or ribonucleoprotein, for example in applications where the Cas protein or ribonucleoprotein complex is utilised to recognise and modify a specific target sequence in a nucleic acid, for instance to mark it as part of a diagnostic test. In such applications, the nuclease activity of the Cas protein may be inactivated and the functional moiety fused to the Cas protein may be a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a particularly preferred aspect, the present invention provides a Cas protein or a ribonucleoprotein complex, wherein the nuclease activity of the Cas protein is inactivated and the at least one functional moiety is a marker protein, for example GFP. In this way it may be possible to specifically target a nucleic acid sequence of interest and to visualize it using a marker which generates an optical signal. Suitable markers may include for example, a fluorescent reporter protein, e.g. Green Fluorescent Protein (GFP), Yellow Fluorescent Protein (YFP), Red Fluorescent Protein (RFP), Cyan Fluorescent Protein (CFP) or mCherry. Such a fluorescent reporter gene provides a suitable marker for visualisation of protein expression since its expression can be simply and directly assayed by fluorescence measurement. Alternatively, the reporter nucleic acid may encode a luminescent protein, such as a luciferase (e.g. firefly luciferase). Alternatively, the reporter gene may be a chromogenic enzyme which can be used to generate an optical signal, e.g. a chromogenic enzyme (such as beta-galactosidase (LacZ) or beta-glucuronidase (Gus)). Reporters used for measurement of expression may also be antigen peptide tags. Other reporters or markers are known in the art, and they may be used as appropriate.

Because the marker may be visualized, in certain embodiments where the target nucleic acid is RNA, specifically mRNA, it may be possible to quantify the transcriptional activity of a gene by detection and quantification of the optical signal provided by the marker, particularly where the optical signal generated by the marker is directly proportionate to the quantity of the expression product. Therefore in preferred embodiments of the invention, Cas proteins or ribonucleoproteins of the invention may be used to assay expression products of a gene of interest.

Throughout, the reference sequences of the Cas proteins of the invention may be defined as a nucleotide sequence encoding the amino acid sequence. For example the amino acid sequence of the motifs defined in SEQ ID's 2 to 6 also includes all nucleic acid sequences which encode that amino acid sequence.

Accordingly, the present invention also provides an isolated nucleic acid molecule encoding a Cas protein comprising;

a. the amino acid motif EKDGKYYC [SEQ ID NO: 2]; and/or
b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
d. the amino acid motif $X_7VYSX_8K$ [SEQ ID NO: 5] wherein $X_7$ is Glutamate or Isoleucine and $X_8$ is one of Tryptophan, Serine or Lysine; and/or
e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;

wherein the Cas protein is capable of DNA cleavage between 50° C. and 100° C. when associated with at least one targeting RNA molecule, and a polynucleotide comprising a target nucleic acid sequence recognised by the targeting RNA molecule.

In another aspect the present invention also provides an isolated nucleic acid molecule encoding a clustered regularly interspaced short palindromic repeat (CRISPR)-associated (Cas) protein having an amino acid sequence of SEQ ID NO: 1 or a sequence of at least 77% identity therewith.

In another aspect the present invention also provides an isolated nucleic acid molecule, further comprising at least one nucleic acid sequence encoding a peptide which upon translation is fused to the Cas protein.

In another aspect the present invention also provides an isolated nucleic acid molecule, wherein the at least one nucleic acid sequence fused to the nucleic acid molecule encoding the Cas protein encodes a protein selected from a helicase, a nuclease, a helicase-nuclease, a DNA methylase, a histone methylase, an acetylase, a phosphatase, a kinase, a transcription (co-)-activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

Expression Vectors

Nucleic acids of the present invention may be isolated. However, in order that expression of the nucleic acid sensing construct may be carried out in a chosen cell, the polynucleotide sequence encoding the Cas protein or ribonucleoprotein will preferably be provided in an expression construct. In some embodiments, the polynucleotide encoding the Cas protein or ribonucleoprotein will be provided as part of a suitable expression vector. In certain embodiments an expression vector of the present invention (with or without nucleotide sequence encoding amino acid residues which on expression will be fused to a Cas protein) may further comprise a nucleotide sequence encoding a targeting RNA molecule as hereinbefore defined. Consequently, such expression vectors can be used in an appropriate host to generate a ribonucleoprotein complex of the invention which can target a desired nucleotide sequence. Alternatively, nucleotide sequences encoding a targeting RNA molecule as hereinbefore defined may be provided in a separate expression vector or alternatively may be delivered to a target cell by other means.

Suitable expression vectors will vary according to the recipient cell and suitably may incorporate regulatory elements which enable expression in the target cell and preferably which facilitate high-levels of expression. Such regulatory sequences may be capable of influencing transcription or translation of a gene or gene product, for example in terms of initiation, accuracy, rate, stability, downstream processing and mobility.

Such elements may include, for example, strong and/or constitutive promoters, 5' and 3' UTR's, transcriptional and/or translational enhancers, transcription factor or protein binding sequences, start sites and termination sequences, ribosome binding sites, recombination sites, polyadenylation sequences, sense or antisense sequences, sequences ensuring correct initiation of transcription and optionally poly-A signals ensuring termination of transcription and transcript stabilisation in the host cell. The regulatory sequences may be plant-, animal-, bacteria-, fungal- or virus derived, and preferably may be derived from the same organism as the host cell. Clearly, appropriate regulatory elements will vary according to the host cell of interest. For example, regulatory elements which facilitate high-level expression in prokaryotic host cells such as in *E. coli* may include the pLac, 17, P(Bla), P(Cat), P(Kat), trp or tac promoters. Regulatory elements which facilitate high-level expression in eukaryotic host cells might include the AOX1 or GAL1 promoter in yeast or the CMV- or SV40-promoters, CMV-enhancer, SV40-enhancer, Herpes simplex virus VIP16 transcriptional activator or inclusion of a globin intron in animal cells. In plants, constitutive high-level expression may be obtained using, for example, the *Zea mays* ubiquitin 1 promoter or 35S and 19S promoters of cauliflower mosaic virus.

Suitable regulatory elements may be constitutive, whereby they direct expression under most environmental conditions or developmental stages, developmental stage specific or inducible. Preferably, the promoter is inducible, to direct expression in response to environmental, chemical or developmental cues, such as temperature, light, chemicals, drought, and other stimuli. Suitably, promoters may be chosen which allow expression of the protein of interest at particular developmental stages or in response to extra- or intra-cellular conditions, signals or externally applied stimuli. For example, a range of promoters exist for use in *E. coli* which give high-level expression at particular stages of growth (e.g. osmY stationary phase promoter) or in response to particular stimuli (e.g. HtpG Heat Shock Promoter).

Suitable expression vectors may comprise additional sequences encoding selectable markers which allow for the selection of said vector in a suitable host cell and/or under particular conditions.

The invention also includes a method of modifying a target nucleic acid in a cell, comprising transfecting, transforming or transducing the cell with any of the expression vectors as hereinbefore described. The methods of transfection, transformation or transduction are of the types well known to a person of skill in the art. Where there is one expression vector used to generate expression of a ribonucleoprotein complex of the invention and when the targeting RNA is added directly to the cell then the same or a different method of transfection, transformation or transduction may be used. Similarly, then there is one expression vector being used to generate expression of a ribonucleoprotein complex of the invention and when another expression vector is being used to generate the targeting RNA in situ via expression, then the same or a different method of transfection, transformation or transduction may be used.

In other embodiments, mRNA encoding the Cas protein or polypeptide is introduced into a cell so that the Cascade complex is expressed in the cell. The targeting RNA which guides the Cas protein complex to the desired target sequence is also introduced into the cell, whether simultaneously, separately or sequentially from the mRNA, such that the necessary ribonucleoprotein complex is formed in the cell.

Accordingly, the invention also provides a method of modifying, i.e. cleaving, tagging, marking or binding, a target nucleic acid comprising contacting the nucleic acid with a ribonucleoprotein complex as hereinbefore defined.

In addition, the invention also includes a method of modifying a target nucleic acid comprising contacting the nucleic acid with a Cas protein or polypeptide as hereinbefore defined, in addition to a targeting RNA molecule as hereinbefore defined.

In accordance with the above methods, modification of target nucleic acid may therefore be carried out in vitro and in a cell-free environment. In a cell-free environment, addition of each of the target nucleic acid, the Cas protein and the targeting RNA molecule may be simultaneous, sequential (in any order as desired), or separately. Thus it is possible for the target nucleic acid and targeting RNA to be added simultaneously to a reaction mix and then the Cas protein or polypeptide of the invention to be added separately at a later stage.

Equally, the modification of the target nucleic acid may be made in vivo, that is in situ in a cell, whether an isolated cell or as part of a multicellular tissue, organ or organism. In the context of whole tissue and organs, and in the context of an organism, the method may desirably be carried out in vivo or alternatively may be carried out by isolating a cell from the whole tissue, organ or organism, treating the cell ribonucleoprotein complex in accordance with the method and subsequently returning the cell treated with ribonucleoprotein complex to its former location, or a different location, whether within the same or a different organism.

In these embodiments, the ribonucleoprotein complex or the Cas protein or polypeptide requires an appropriate form of delivery into the cell. Such suitable delivery systems and methods are well known to persons skilled in the art, and include but are not limited to cytoplasmic or nuclear microinject on. In preferred modes of delivery, an Adeno-associated virus (AAV) is used; this delivery system is not disease causing in humans and has been approved for clinical use in Europe.

Accordingly the present invention provides a method of modifying a target nucleic acid comprising contacting the nucleic acid with:

a. a ribonucleoprotein complex as hereinbefore defined; or b. a protein or protein complex as hereinbefore defined and an RNA molecule as as hereinbefore defined.

In a further aspect the present invention provides a method of modifying a target nucleic acid in a cell, comprising transforming, transfecting or transducing the cell with an expression vector comprising nucleotide sequences encoding a ribonucleoprotein complex as hereinbefore defined; or alternatively transforming, transfecting or transducing the cell with an expression vector comprising nucleotide sequences encoding a protein or protein complex as hereinbefore defined and a further expression vector comprising a nucleotide sequence encoding a targeting RNA molecule as hereinbefore defined.

In a further aspect, the present invention provides a method of modifying a target nucleic acid in a cell comprising transforming, transfecting or transducing the cell with an expression vector comprising nucleotide sequences encoding a protein or protein complex as hereinbefore defined, and then delivering a targeting RNA molecule as hereinbefore defined into the cell.

In embodiments where the guide (i.e. targeting) RNA (gRNA) molecule and the Cas protein or polypeptide are provided separately rather than as part of a ribonucleoprotein complex, the gRNA molecule requires an appropriate form of delivery into a cell, whether simultaneously, separately or sequentially with the Cas protein or protein complex. Such forms of introducing RNA into cells are well known to a person of skill in the art and may include in vitro or ex vivo delivery via conventional transfection methods. Physical methods, such as microinjection and electroporation, as well as calcium co-precipitation, and commercially available cationic polymers and lipids, and cell-penetrating peptides, cell-penetrating (biolistic) particles may each be used. For example, viruses, particularly preferred is AAV, may be used as delivery vehicles, whether to the cytoplasm and/or nucleus, for example via the (reversible) fusion of Cas protein complex of the invention or a ribonucleoprotein complex of the invention to the viral particle.

In another aspect the present invention provides a method of modifying a target nucleic acid, wherein the at least one functional moiety is a marker protein or reporter protein and the marker protein or reporter protein associates with the target nucleic acid; preferably wherein the marker is a fluorescent protein, for example a green fluorescent protein (GFP).

In the aforementioned methods of modifying a target nucleic acid, the functional moiety may be a marker and the marker associates with the target nucleic acid; preferably wherein the marker is a protein; optionally a fluorescent protein, e.g. green fluorescent protein (GFP), yellow fluorescent protein (YFP), red fluorescent protein (RFP) or mCherry. Whether in vitro, ex vivo or in vivo, then methods of the invention can be used to directly visualize a target locus in a nucleic acid molecule, preferably in the form of a higher order structure such as a supercoiled plasmid or chromosome, or a single stranded target nucleic acid such as mRNA. Direct visualisation of a target locus may use electron micrography, or fluorescence microscopy. However, it will be appreciated that in the context of methods of the invention, other kinds of label may be used as the marker including organic dye molecules, radiolabels and spin labels which may be small molecules.

In methods of the invention for modifying a target nucleic acid wherein the target nucleic acid is dsDNA, the functional moiety may be a nuclease or a helicase-nuclease, and the modification is preferably a single stranded or a double stranded break at a desired locus. In this way unique sequence specific cutting of DNA can be engineered by using a suitable functional moiety fused to a ribonucleoprotein complex. The chosen sequence of the RNA component of the final ribonucleoprotein complex provides the desired sequence specificity for the action of the functional moiety.

Therefore, the invention also provides a method of non-homologous end joining of a dsDNA molecule in a cell at a desired locus to remove at least a part of a nucleotide sequence from the dsDNA molecule; optionally to knockout the function of a gene or genes, wherein the method comprises making double stranded breaks using any of the methods of modifying a target nucleic acid as hereinbefore described.

The invention further provides a method of homologous recombination of a nucleic acid into a dsDNA molecule in a cell at a desired locus in order to modify an existing nucleotide sequence or insert a desired nucleotide sequence, wherein the method comprises making a double stranded break at the desired locus using any of the methods of modifying a target nucleic acid as hereinbefore described.

The invention therefore also provides a method of modifying gene expression in an organism comprising modifying a target nucleic acid sequence according to any of the methods hereinbefore described, wherein the nucleic acid is dsDNA and the functional moiety is selected from a DNA modifying enzyme (e.g. a methylase or acetylase), a transcription activator or a transcription repressor.

The invention additionally provides a method of modifying gene expression in an organism comprising modifying a target nucleic acid sequence according to any of the methods hereinbefore described, wherein the nucleic acid is an mRNA and the functional moiety is a ribonuclease; optionally selected from an endonuclease, a 3' exonuclease or a 5' exonuclease.

In any aspect of methods of the invention described herein, the target nucleic acid may be DNA, RNA or synthetic nucleic acid. Preferably the target nucleic acid is DNA; preferably dsDNA.

However, the target nucleic acid can be RNA; preferably mRNA. Alternatively therefore, the present invention also provides methods of modifying a target nucleic acid, wherein the target nucleic acid is RNA.

In another aspect the present invention provides a method of modifying a target nucleic acid, wherein the nucleic acid is dsDNA, the at least one functional moiety is a nuclease or a helicase-nuclease, and the modification is a single-stranded or a double-stranded break at a desired locus.

In another aspect the present invention provides a method of modifying a target nucleic acid in a cell, wherein modification results in a silencing of gene expression at a desired locus; and wherein the method includes the steps of;
 a. making double-stranded breaks in the dsDNA molecule; and
 b. repair of the dsDNA molecule in the cell by non-homologous end joining (NHEJ).

In another aspect the present invention provides a method of modifying a target nucleic acid in a cell; wherein the existing nucleotide sequence is modified or deleted and/or a desired nucleotide sequence is inserted at a desired location wherein the method includes the steps of;
 a. making a double stranded break at the desired locus; and
 b. repair of the dsDNA molecule in the cell by homologous recombination.

In another aspect the present invention provides a method of modifying gene expression in a cell comprising modifying a target nucleic acid sequence as hereinbefore described; wherein the nucleic acid is dsDNA and the functional moiety is selected from a DNA modifying enzyme (e.g. a methylase or acetylase), a transcription activator or a transcription repressor.

In another aspect the present invention provides a method of modifying gene expression in a cell comprising modifying a target nucleic acid sequence as hereinbefore described, wherein the nucleic acid is an mRNA and the functional moiety is a ribonuclease; optionally selected from an endonuclease, a 3' exonuclease or a 5' exonuclease.

In another aspect the present invention provides a method of modifying a target nucleic acid as hereinbefore described, wherein the method is carried out at a temperature between 50° C. and 100° C. Preferably, the method is carried out at a temperature at or above 60° C. More preferably, the method is carried out at a temperature between 60° C. and 80° C. Optimally, the method is carried out at a temperature between 60° C. and 65° C.

In any of the methods of modifying a target nucleic acid hereinbefore described, the cell may be a prokaryotic cell or alternatively, may be a eukaryotic cell.

Host Cells

Advantageously, the present invention is of broad applicability and host cells of the present invention may be derived from any genetically tractable organism which can be cultured. Accordingly, the present invention provides a host cell transformed by a method as hereinbefore described.

Appropriate host cells may be prokaryotic or eukaryotic. In particular, commonly used host cells may be selected for use in accordance with the present invention including prokaryotic or eukaryotic cells which are genetically accessible and which can be cultured, for example prokaryotic cells, fungal cells, plant cells and animal cells including human cells (but not embryonic stem cells). Preferably, host cells will be selected from a prokaryotic cell, a fungal cell, a plant cell, a protist cell or an animal cell. Preferred host cells for use in accordance with the present invention are commonly derived from species which typically exhibit high growth rates, are easily cultured and/or transformed, display short generation times, species which have established genetic resources associated with them or species which have been selected, modified or synthesized for optimal expression of heterologous protein under specific conditions. In preferred embodiments of the invention where the protein of interest is eventually to be used in specific industrial, agricultural, chemical or therapeutic contexts, an appropriate host cell may be selected based on the desired specific conditions or cellular context in which the protein of interest is to be deployed. Preferably the host cell will be a prokaryotic cell. In preferred embodiments the host cell is a bacterial cell. The host cell may for instance be an *Escherichia coli* (*E. coli*) cell. Preferably the host cell will be a cell of a thermophilic bacterium.

BRIEF DESCRIPTION OF THE FIGURES

The invention will now be described in detail with reference to a specific embodiment and with reference to the accompanying drawings, in which.

Figure 1:
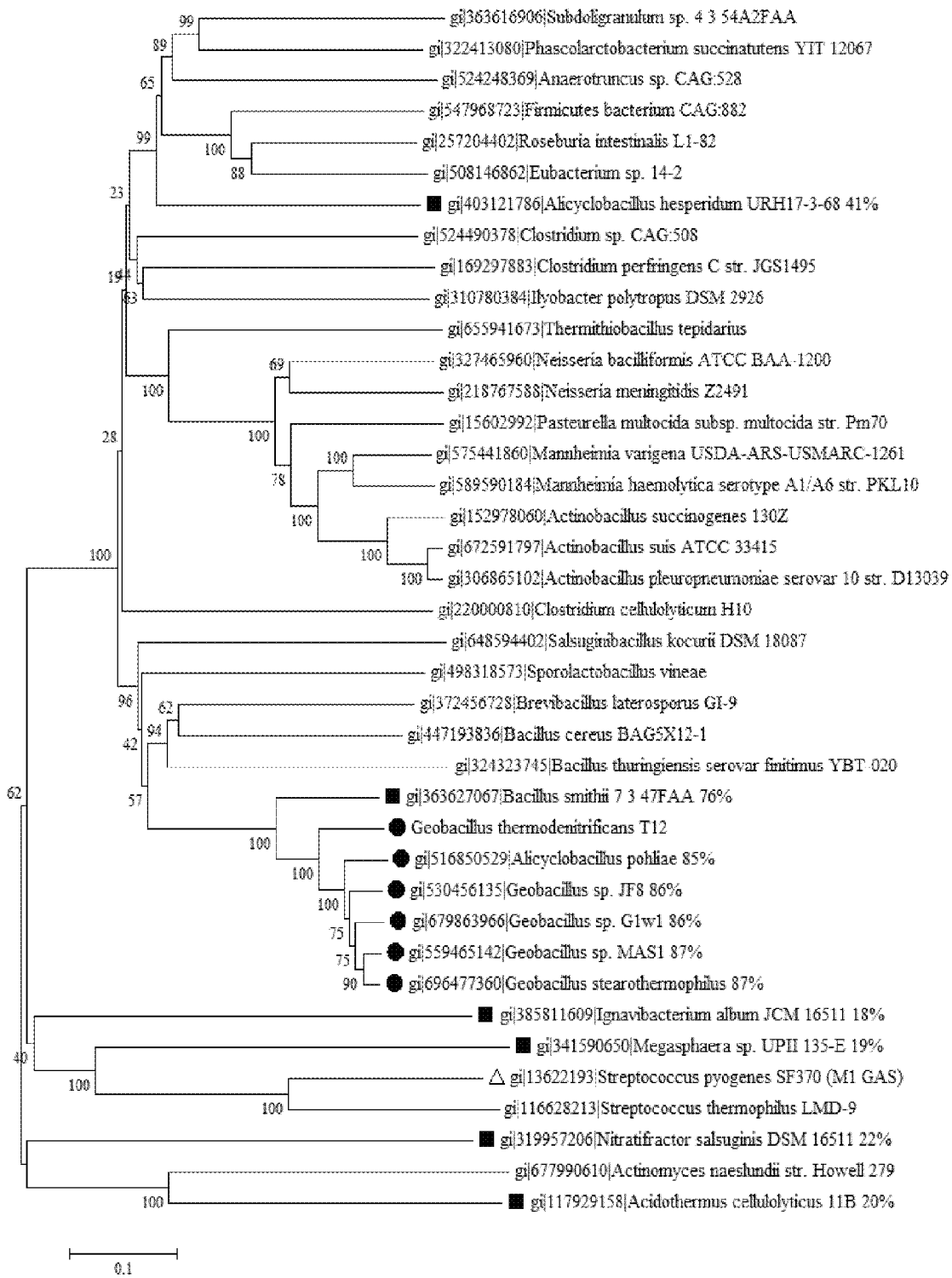
FIG. 1 shows a Neighbour-Joining tree of Cas9 protein sequences. All sequences having a sequence similarity above 40% with strain T12 based on pBLAST or PSI-BLAST were included, as well as currently well-characterized sequences (*S. pyogenes, S. thermophiles* and *A. naeslundii*), as well as all currently identified thermophilic sequences also when these were below 40% identity. For all thermophilic sequences, the percentage identity to T12 is indicated after the strain name. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values; scale bar represents estimated amino acid substitutions per site.

Below are polynucleotide and amino acid sequences of Cas proteins used in accordance with the invention.

*Geovacillus thermodenitrificans* T12 Cas9 protein AA sequence

[SEQ ID NO: 1]
MKYKIGLDIGITSIGWAVINLDIPRIEDLGVRIFDRAENPKTGESLALPR

RLARSARRRLRRRKHRLERIRRLFVREGILTKEELNKLFEKKHEIDVWQL

RVEALDRKLNNDELARILLHLAKRRGFRSNRKSERTNKENSTMLKHIEEN

QSILSSYRTVAEMVVKDPKFSLHKRNKEDNYTNTVARDDLEREIKLIFAK

QREYGNIVCTEAFEHEYISIWASQRPFASKDDIEKKVGFCTFEPKEKRAP

KATYTFQSFTVWEHINKLRLVSPGGIRALTDDERRLIYKQAFHKNKITFH

DVRTLLNLPDDTRFKGLLYDRNTTLKENEKVRFLELGAYHKIRKAIDSVY

GKGAAKSFRPIDFDTFGYALTMFKDDTDIRSYLRNEYEQENGKRMENLAD

KVYDEELIEELLNLSFSKFGHLSLKALRNILPYMEQGEVYSTACERAGYT

FTGPKKKQKTVLLPNIPPIANPVVMRALTQARKVVNAIIKKYGSPVSIHI

ELARELSQSFDERRKMQKEQEGFNRKKNETARIQLVEYGLTLNPTGLDIV

KFKLWSEQNGKCAYSLQPIEIERLLEPGYTEVDHVIPYSRSLDDSYTNKV

LVLTKENREKGNRTPAEYLGLGSERWQQFETFVLTNKQFSKKKRDRLLRL

HYDENEENEFKNRNLNDTRYISRFLANFIREHLKFADSDDKQKVYTVNGR

ITAHLRSRWNFNKNREESNLHHAVDAAIVACTTPSDIARVTAFYQRREQN

KELSKKTDPQFPQPWPHFADELQARLSKNPKESIKALNLGNYDNEKLESL

QPVGVSRMPKRSITGAAHQETLRRYIGIDERSGKIQTVVKKKLSEIQLDK

TGHFPMYGKESDPRTYEAIRQRLLEHNNDPKKAFQEPLYKPKKNGELGPI

IRTIKIIDTTVQVIPLNDGKTVAYNSNIVRVDVFEKDGKYYCVPIYTIDM

MKGILPNKAIEPNKPYSEWKEMTEDYTFRFSLYPNDLIRIEFPREKTIKT

AVGEEIKIKDLFAYYQTIDSSNGGLSLVSHDNNFSLRSIGSRTLKRFEKY

QVDVLGNIYKVRGEKRVGVASSSHSKAGETIRPL*

*Geovacillus thermodenitrificans* T12 Cas9 DNA Sequence

[SEQ ID NO: 7]
ATGAAGTATAAAATCGGTCTTGATATCGGCATTACGTCTATCGGTTGGGC

TGTCATTAATTTGGACATTCCTCGCATCGAAGATTTAGGTGTCCGCATTT

TTGACAGAGCGGAAAACCCGAAAACCGGGGAGTCACTAGCTCTTCCACGT

CGCCTCGCCCGCTCCGCCCGACGTCGTCTGCGGCGTCGCAAACATCGACT

GGAGCGCATTCGCCGCCTGTTCGTCCGCGAAGGAATTTTAACGAAGGAAG

AGCTGAACAAGCTGTTTGAAAAAAAGCACGAAATCGACGTCTGGCAGCTT

CGTGTTGAAGCACTGGATCGAAAACTAAATAACGATGAATTAGCCCGCAT

CCTTCTTCATCTGGCTAAACGGCGTGGATTTAGATCCAACCGCAAGAGTG

AGCGCACCAACAAAGAAAACAGTACGATGCTCAAACATATTGAAGAAAAC

CAATCCATTCTTTCAAGTTACCGAACGGTTGCAGAAATGGTTGTCAAGGA

TCCGAAATTTTCCCTGCACAAGCGTAATAAAGAGGATAATTACACCAACA

CTGTTGCCCGCGACGATCTTGAACGGGAAATCAAACTGATTTTCGCCAAA

CAGCGCGAATATGGGAACATCGTTTGCACAGAAGCATTTGAACACGAGTA

TATTTCCATTTGGGCATCGCAACGCCCTTTTGCTTCTAAGGATGATATCG

AGAAAAAAGTCGGTTTCTGTACGTTTGAGCCTAAAGAAAAACGCGCGCCA

AAAGCAACATACACATTCCAGTCCTTCACCGTCTGGGAACATATTAACAA

ACTTCGTCTTGTCTCCCCGGGAGGCATCCGGGCACTAACCGATGATGAAC

GTCGTCTTATATACAAGCAAGCATTTCATAAAAATAAAATCACCTTCCAT

GATGTTCGAACATTGCTTAACTTGCCTGACGACACCCGTTTTAAAGGTCT

TTTATATGACCGAAACACCACGCTGAAGGAAAATGAGAAAGTTCGCTTCC

TTGAACTCGGCGCCTATCATAAAATACGGAAAGCGATCGACAGCGTCTAT

GGCAAAGGAGCAGCAAAATCATTTCGTCCGATTGATTTTGATACATTTGG

CTACGCATTAACGATGTTTAAAGACGACACCGACATTCGCAGTTACTTGC

GAAACGAATACGAACAAAATGGAAAACGAATGGAAAATCTAGCGGATAAA

```
GTCTATGATGAAGAATTGATTGAAGAACTTTTAAACTTATCGTTTTCTAA

GTTTGGTCATCTATCCCTTAAAGCGCTTCGCAACATCCTTCCATATATGG

AACAAGGCGAAGTCTACTCAACCGCTTGTGAACGAGCAGGATATACATTT

ACAGGGCCAAAGAAAAAACAGAAAACGGTATTGCTGCCGAACATTCCGCC

GATCGCCAATCCGGTCGTCATGCGCGCACTGACACAGGCACGCAAAGTGG

TCAATGCCATTATCAAAAGTACGGCTCACCGGTCTCCATCCATATCGAA

CTGGCCCGGGAACTATCACAATCCTTTGATGAACGACGTAAAATGCAGAA

AGAACAGGAAGGAAACCGAAAGAAAAACGAAACTGCCATTCGCCAACTTG

TTGAATATGGGCTGACGCTCAATCCAACTGGGCTTGACATTGTGAAATTC

AAACTATGGAGCGAACAAAACGGAAATGTGCCTATTCACTCCAACCGAT

CGAAATCGAGCGGTTGCTCGAACCAGGCTATACAGAAGTCGACCATGTGA

TTCCATACAGCCGAAGCTTGGACGATAGCTATACCAATAAAGTTCTTGTG

TTGACAAAGGAGAACCGTGAAAAAGGAAACCGCACCCCAGCTGAATATTT

AGGATTAGGCTCAGAACGTTGGCAACAGTTCGAGACGTTTGTCTTGACAA

ATAAGCAGTTTTCGAAAAAGAAGCGGGATCGACTCCTTCGGCTTCATTAC

GATGAAAACGAAGAAAATGAGTTTAAAAATCGTAATCTAAATGATACCCG

TTATATCTCACGCTTCTTGGCTAACTTTATTCGCGAACATCTCAAATTCG

CCGACAGCGATGACAAACAAAAAGTATACACGGTCAACGGCCGTATTACC

GCCCATTTACGCAGCCGTTGGAATTTTAACAAAAACCGGGAAGAATCGAA

TTTGCATCATGCCGTCGATGCTGCCATCGTCGCCTGCACAACGCCGAGCG

ATATCGCCCGAGTCACCGCCTTCTATCAACGGCGCGAACAAAACAAAGAA

CTGTCCAAAAGACGGATCCGCAGTTTCCGCAGCCTTGGCCGCACTTTGC

TGATGAACTGCAGGCGCGTTTATCAAAAAATCCAAAGGAGAGTATAAAAG

CTCTCAATCTTGGAAATTATGATAACGAGAAACTCGAATCGTTGCAGCCG

GTTTTTGTCTCCCGAATGCCGAAGCGGAGCATAACAGGAGCGGCTCATCA

AGAAACATTGCGGCGTTATATCGGCATCGACGAACGGAGCGGAAAAATAC

AGACGGTCGTCAAAAAGAAACTATCCGAGATCCAACTGGATAAAACAGGT

CATTTCCCAATGTACGGGAAAGAAAGCGATCCAAGGACATATGAAGCCAT

TCGCCAACGGTTGCTTGAACATAACAATGACCCAAAAAAGGCGTTTCAAG

AGCCTCTGTATAAACCGAAGAAGAACGGAGAACTAGGTCCTATCATCCGA

ACAATCAAAATCATCGATACGACAAATCAAGTTATTCCGCTCAACGATGG

CAAAACAGTCGCCTACAACAGCAACATCGTGCGGGTCGACGTCTTTGAGA

AAGATGGCAAATATTATTGTGTCCCTATCTATACAATAGATATGATGAAA

GGGATCTTGCCAAACAAGGCGATCGAGCCGAACAAACCGTACTCTGAGTG

GAAGGAAATGACGGAGGACTATACATTCCGATTCAGTCTATACCCAAATG

ATCTTATCCGTATCGAATTTCCCCGAGAAAAACAATAAAGACTGCTGTG

GGGGAGAAATCAAAATTAAGGATCTGTTCGCCTATTATCAAACCATCGAC

TCCTCCAATGGAGGGTTAAGTTTGGTTAGCCATGATAACAACTTTTCGCT

CCGCAGCATCGGTTCAAGAACCCTCAAACGATTCGAGAAATACCAAGTAG

ATGTGCTAGGCAACATCTACAAAGTGAGAGGGGAAAAGAGAGTTGGGGTG

GCGTCATCTTCTCATTCGAAAGCCGGGGAAACTATCCGTCCGTTATAA
```

DETAILED DESCRIPTION

Example 1: Isolation of *G. thermodenitrificans*

*G. thermodenitrificans* was surprisingly discovered during a search of a library of ±500 isolates for a thermophile capable of degrading lignocellulosic substrates under anaerobic conditions. At first a library of ±500 isolates was established which, after several selection rounds by isolation on cellulose and xylan, was trimmed down to 110 isolates. This library of 110 isolates consisted solely of *Geobacillus* isolates with *G. thermodenitrificans* representing 79% of the library.

The isolated *G. thermodenitrificans* strain has been named "T12".

Example 2: Defining the Essential Consensus Sequences for Cas9 in *Geobacillus thermodenitrificans*

The following database searches and alignments were performed:

pBLAST and nBLAST were performed on the in-house BLAST server, in which either the protein or gene sequence of *G. thermodenitrificans* T12 was used as query sequence. This database was last updated May 2014 and therefore does not contain the most recently added *Geobacillus* genomes, but normal online BLAST was not used to prevent publication of the T12 sequence. See Appendix 1 for the results of the in-house pBLAST in Excel format, the most relevant sequences of this (sequence identities greater than 40% are included in FIG. 1).

To include more recent sequence data, the sequence of *Geobacillus* MAS1 (most closely related to T12 Cas9) was used to perform a PSI-BLAST on the NCBI website (Johnson et al., 2008 Nucleic Acids Res. 36 (Web Server issue): W5-9). Two consecutive rounds of PSI-BLAST were performed, in which only sequences that met the following criteria were used for the next round: minimum sequence coverage of 96% in the first round and 97% in the second and third round, minimum identity 40%, only one strain per species.

The sequences resulting from the PSI-BLAST, as well as the sequences with more than 40% identity to T12 from the internal server pBLAST that did not appear in the PSI-BLAST were aligned together with currently well-characterized mesophilic sequences and all currently identified thermophilic sequences also if these were more distantly related, from which a Neighbour-Joining tree was constructed (see FIG. 1). Alignment was performed in Mega6 using ClustalW, after which a tree was constructed using the Neighbour-Joining method and bootstrap analysis was performed using 1000 replicates.

Figure 2:
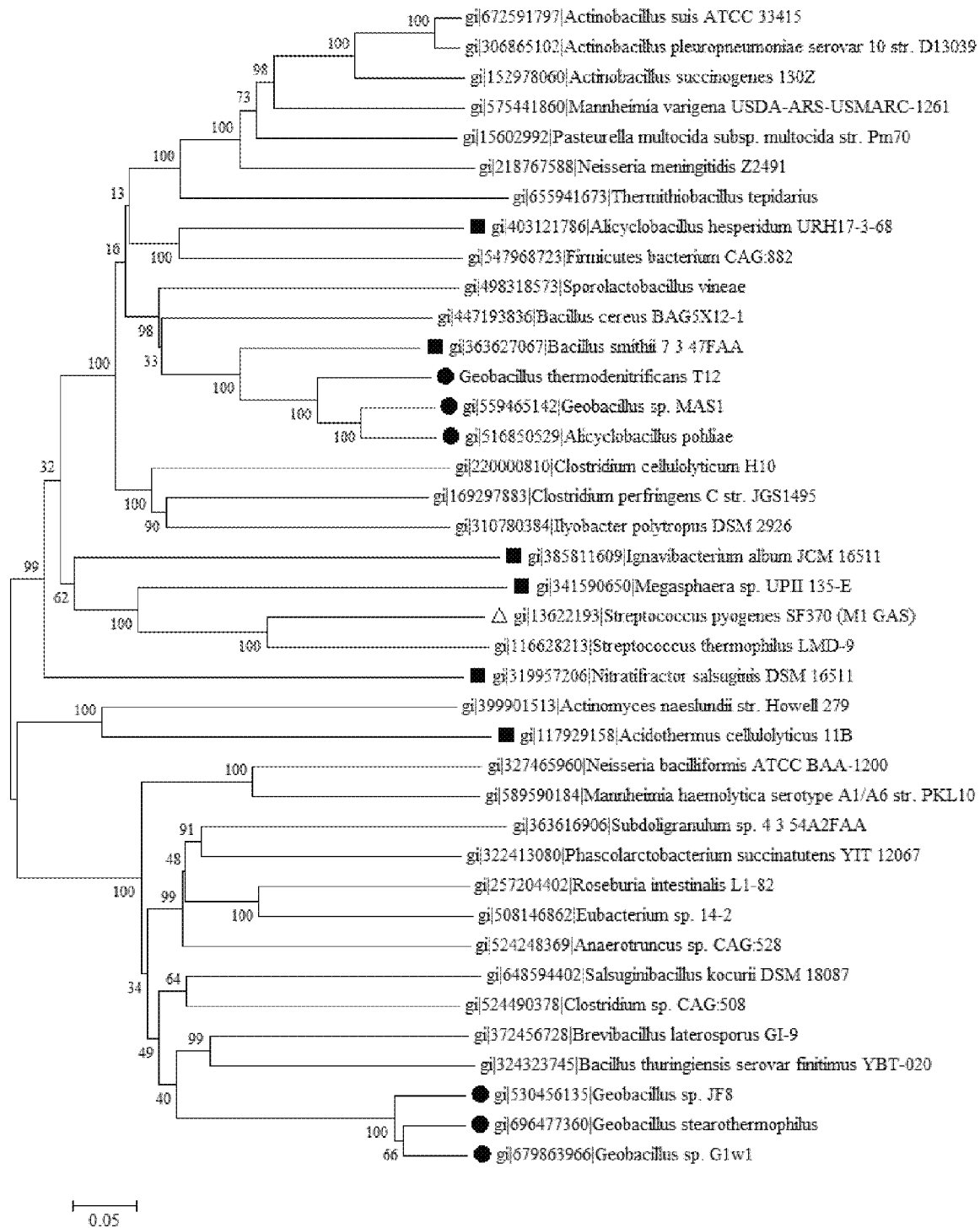
FIG. 2 shows a Neighbour-Joining tree of Cas9 gene sequences. Identity at the gene level was extremely poor; sequences from the same organisms as those used for the protein alignment were used for the gene alignment. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values.

When BLASTn was performed using *Geobacillus* sp. MAS1 as the query sequence, only *Geobacillus* sp. JF8 Cas9 was identified with 88% identity, indicating very little homology at the gene level. FIG. 2 is a Neighbour-Joining tree of Clustal-aligned Cas9 gene sequences.

Protein sequences of *G. thermodenitrificans* T12, *A. naeslundii* and *S. pyogenes* were further analyzed for protein domain homology (see FIG. 3) by aligning them in Clone-Manager using BLOSUM62 with default settings.

Figure 3:
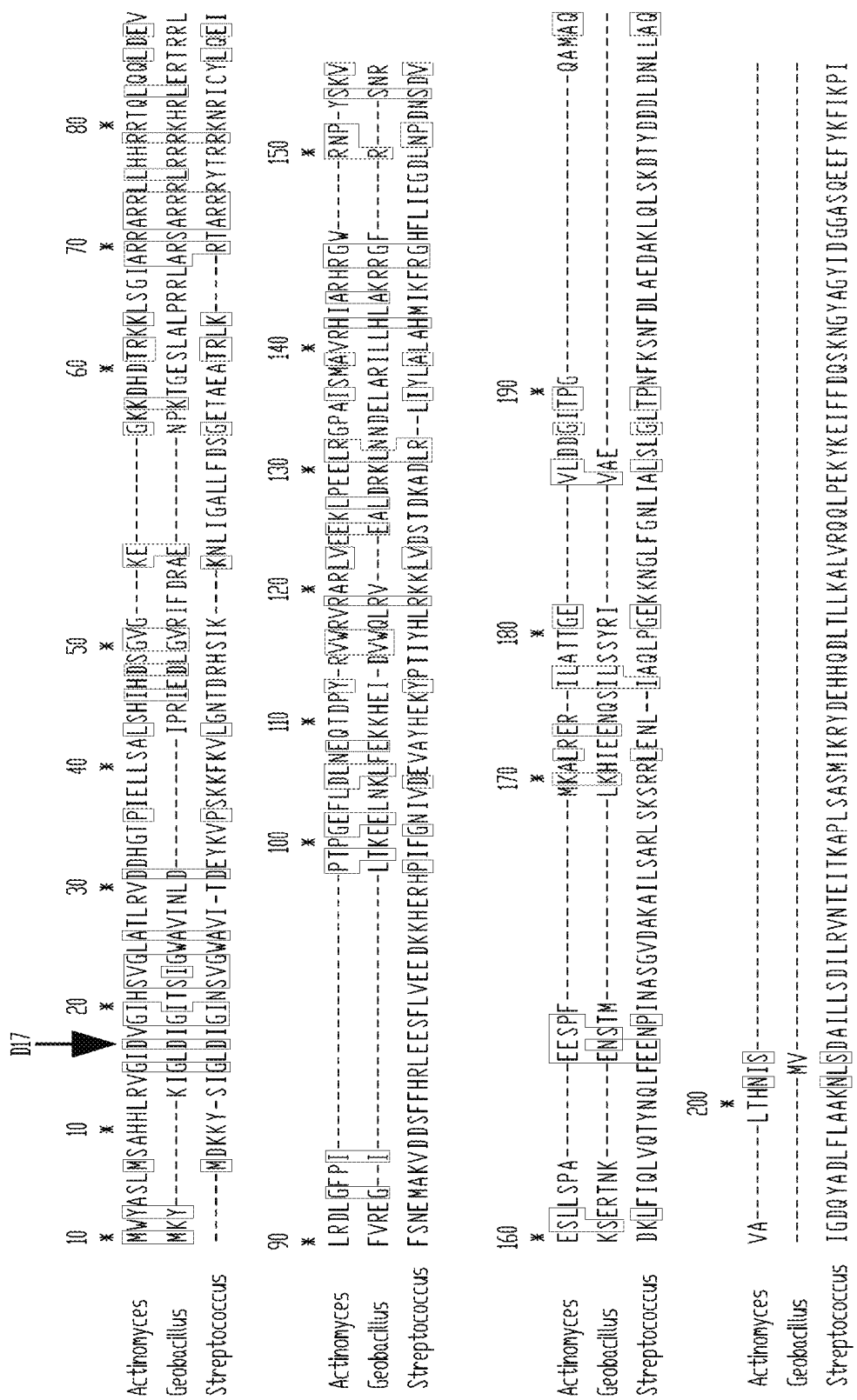
FIG. 3 shows a protein sequence alignment for T12-Cas9 (SEQ ID NO: 1) (Type II-C) with well-characterized Type II-C (*A. naeslundii*/'ana'; SEQ ID NO: 8) and Type II-A (*S. pyogenes*/'pyo'; SEQ ID NO: 9 and *S. thermophilus*) Cas9 sequences. Important active site residues are well conserved and indicated with black arrows. Protein domains as described for Ana-Cas9 and Pyo-Cas9 (Jinek, et al., 2014, Science 343: 1247997) are indicated with shaded boxes and similarly coloured letters. The PAM recognition domain has been determined for the *S. pyogenes* Type II-A system but not for any Type II-C system and is therefore only indicated in the *S. pyogenes* sequence.
Figure 3:
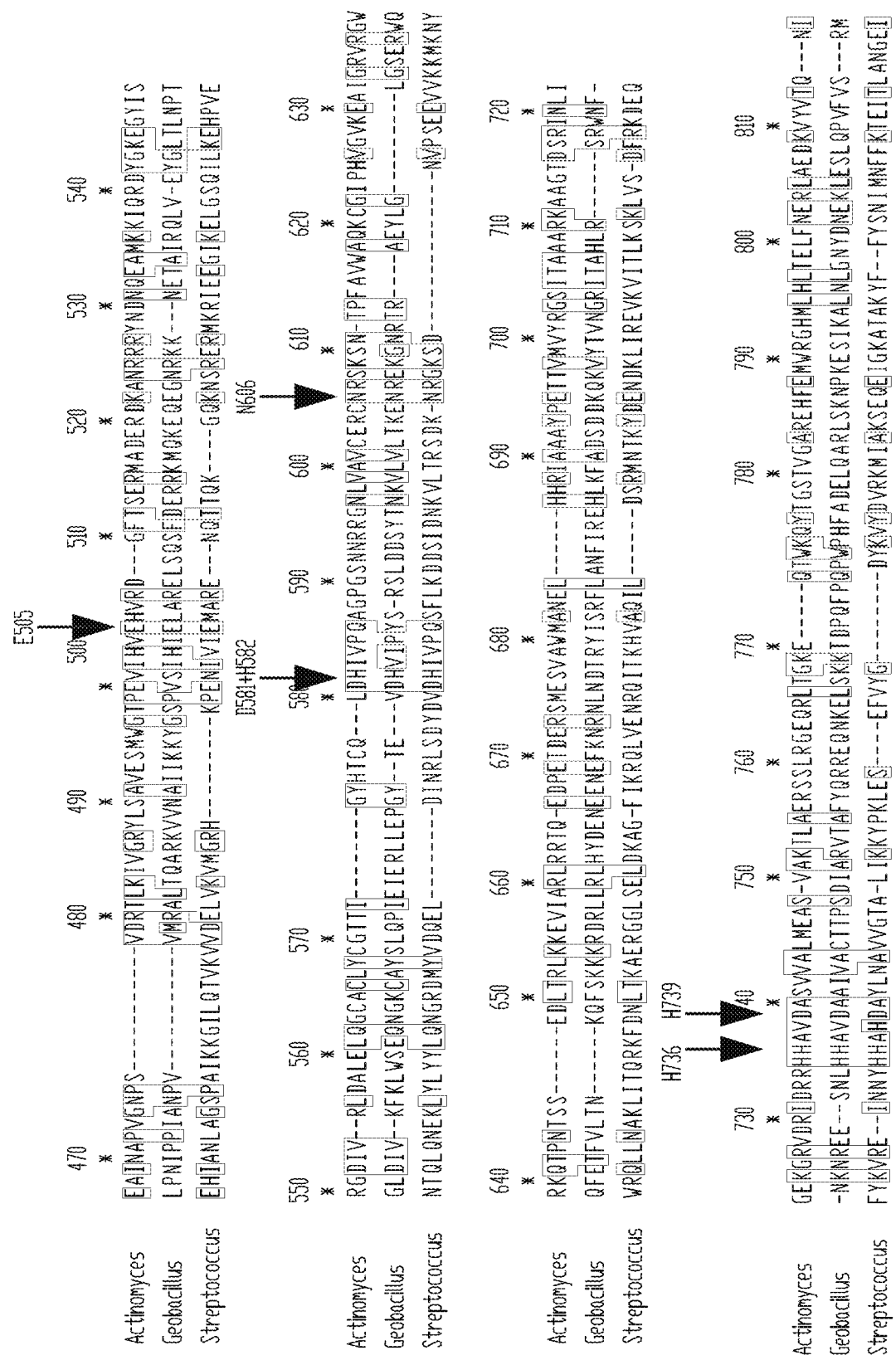
Figure 3:
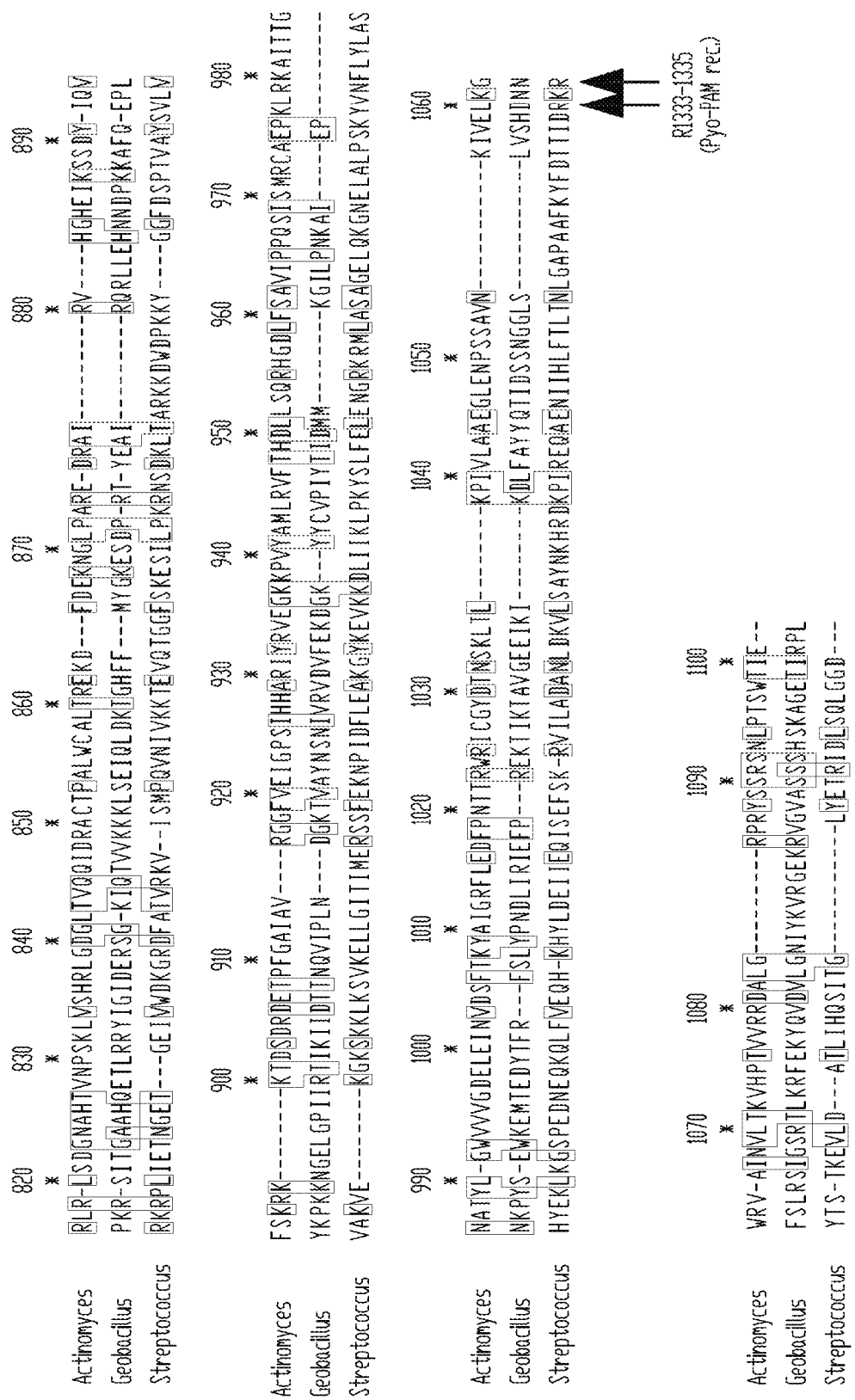
Figure 4:
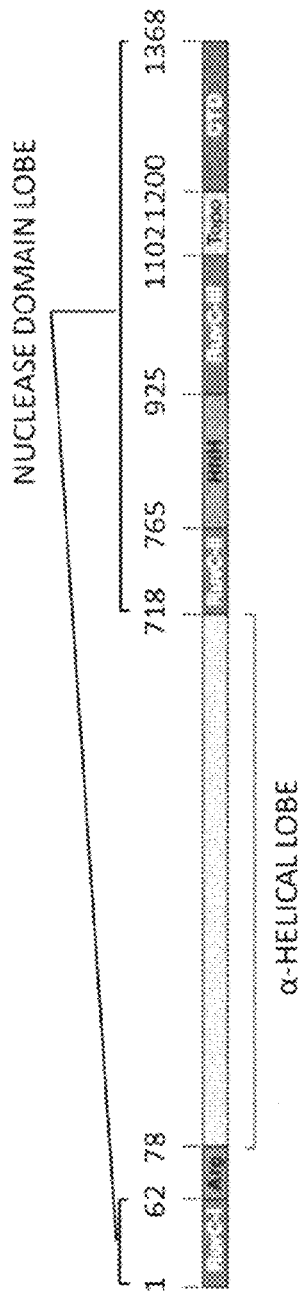
FIG. 4 shows protein architecture of *A. naeslundii* Cas9 (Cas9-Ana) (Jinek et al., 2014). T12-Cas9 belongs to the same Type II-C CRISPR system and active site residues could be identified.
Figure 5:
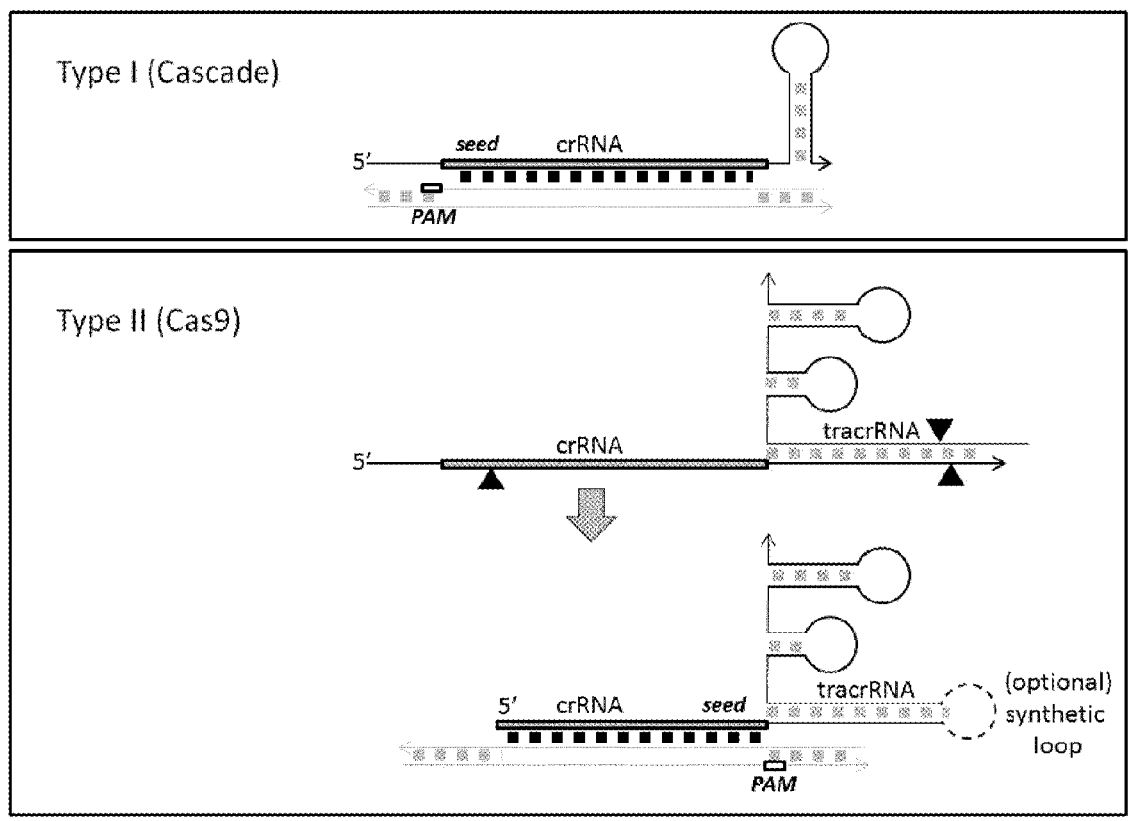
FIG. 5 shows a comparison of crRNA-guided targeting of complementary dsDNA. Base pairing is indicated with dashed lines. RNA is depicted in black, DNA in grey. Base pairing between crRNA spacer and target protospacer is indicated with thick black dashed line, base pairing between DNA strands and between RNA strands is indicated with thick grey dashed lines. The 5' end of the crRNA is indicated. Note that PAM (small white box) in Type I resides downstream of target strand (protospacer), whereas in Type II it resides at the other end on the displaced strand. Likewise, the seed (the predicted sequence of the guide where base pairing with target DNA strand starts, and where no mismatches are allowed) is located close to the PAM, and as such differs in types I and II (Van der Oost, 2014 ibid.). Panel A shows a schematic of a Type I Cascade system of *E. coli*. crRNA has internal spacer (grey box, 31-32 nt that allows for target recognition), flanked bt a 8 nt 5' handle and a 29 nt 3' handle that consists of a stem-loop structure (hairpin) (Jore 2011 ibid.). Panel B shows a schematic of a Type II Cas9 system of *S. pyogenes*. crRNA basepairs with tracrRNA, that allows for processing by RNaseIII (opposite black triangles). Additionally, the 5' end of the crRNA is trimmed by an RNase (black triangle), typically resulting in a 20 nt spacer. Note that a synthetic loop may be introduced to link the crRNA and tracrRNA, resulting in a single guide RNA (sgRNA) (Jinek et al., 2012 ibid.).

Example 3: Identifying Core Amino Acid Motifs which are Essential for the Function of CAS9 and Those which Confer Thermostability in Thermophilic Cas9 Nucleases Percentages identity of the above described aligned protein sequences are provided in FIG. 1. T12-Cas9 belongs to Type II-C. The best-studied and recently crystalized structure of a Type II-C system is from *Actinomyces naeslundii* (Jinek et al., 2014, Science 343: 1247997). This protein sequence shows only 20% identity to T12-Cas9 but can be used to estimate highly conserved residues. Two well-characterized Type II-A systems (*S. pyogenes* and *S. thermophilus*) were also included in the analyses (Jinek et al., 2014, Science 343: 1247997; Nishimasu et al., 2014, Cell 156: 935-949). Alignments of these four protein sequences are shown in FIG. 3; FIG. 4 shows the protein architecture as determined for *A. naeslundii* ('Ana-Cas9') (Jinek et al., 2014, Science 343: 1247997). The length of Cas9 from t12 and *Actinomyces naeslundii* is highly similar (*A. naeslundii* 1101 aa, T12 1082 aa) and T12 is expected to have similar protein architecture but this remains to be determined, as the overall sequence identity to cas9-Ana is only 20%. All active side residues described by Jinek et al. (Jinek et al., 2014, Science 343: 1247997) in Cas9 from *A. naeslundii* and *S. pyogenes* could be identified in T12-Cas9 (see FIG. 3). The PAM-binding domain has been determined for the *S. pyogenes* Type II-A system but not for any Type II-C system and is therefore only indicated in the *S. pyogenes* sequence. Moreover, the PAM-recognition site varies strongly, not only between CRISPR systems but also between species containing the same system. For more information on the PAM please see question 4 and future planning.

Example 4: Determination of the PAM Sequence of *G. thermodenitrificans* T12 Cas9

It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10: 957-963.).

Cas9 proteins function as sequence-specific nucleases for the type II CRISPR systems (Makarova et al., 2011, Nat Rev Micro 9: 467-477). Small crRNA molecules, which consist of a "spacer" (target) linked to a repetition region, are the transcription and processing products of a CRISPR loci. "Spacers" naturally originate from the genome of bacteriophages and mobile genetic elements, but they can also be designed to target a specific nucleotide sequence during a genetic engineering process (Bikard et al., 2013, Nucleic Acids Research 41: 7429-7437). The crRNA molecules are employed by the Cas9 as guides for the identification of their DNA targets. The spacer region is identical to the targeted for cleavage DNA region, the "protospacer" (Brouns et al., 2012, Science 337: 808-809). A PAM (Protospacer Adjacent Motif), next to the protospacer, is required for the recognition of the target by the Cas9 (Jinek et al., 2012, Science 337: 816-821).

Example 5: Target Generation with Randomized PAM

Two different spacers from the CRISPR II loci of the *G. thermodenitrificans* T12 strain were amplified by PCR using the *G. thermodenitrificans* T12 genomic DNA as template. Two pairs of degenerate primers were used for the amplification of each spacer:

Firstly, a pair that cause the introduction of six random nucleotides upstream of the "protospacer" fragment were used, leading to the production of a pool of protospacers with randomized PAM sequences.

Secondly, a pair that cause the introduction of six random nucleotides downstream of the "protospacer" fragment were used, leading to the production of a pool of protospacers with randomized PAM sequences.

The produced fragments were ligated to the pNW33n vector, producing 4 pools of "protospacer" constructs, with all the possible 4096 different combinations of 6-nucleotide long PAMs each. The assembled DNA was used for the transformation of *G. thermodenitrificans* T12 cells. The cells were plated on chloramphenicol selection and more than $2 \times 10^6$ cells from each protospacer pool will be pooled. The plasmid DNA was extracted from the pools, the target region will be PCR amplified and the products sent for deep sequencing. The PAMs with the fewest reads will be considered active and the process will be repeated only with pNW33n constructs that contain spacers with these PAMs. Reduced transformation efficiency of the *G. thermodenitrificans* T12 will confirm the activity of the PAMs.

Example 6. Functional Temperature Ranges for *Geobacillus thermodenitrificans* Cas9

No temperature range experiments have been conducted to date on any publically available Cas9 protein. The Cas9 proteins used in research all have a mesophilic origin with a maximum growth temperature of 45° C. for the host organism *Streptococcus pyogenes* (ATCC_700294).

Here the range of temperatures within which Cas9 from *Geobacillus thermodenitrificans* is stable and functional and further the temperature at which its activity is optimal was experimentally determined. Furthermore, the functional and preferred temperatures ranges for Cas9 nucleases from other *Geobacillus* species were also determined.

Temperature ranges of *Geobacillus thermodenitrificans* T12 Cas9 nucleases have been determined in vitro by using a single guide RNA (sgRNA). The sgRNA consists of the endogenous bacterial crRNA and tracrRNA into a single chimeric transcript and has been created by making use of the pT7 cloning vector containing the crRNA:tracrRNA backbone, preceded by a 20 basepair (bp) target sequence (Jao et al., 2013, PNAS 110: 13904-13909). The target sequence starts with the 20 bp target and ends with the T12 PAM sequence (derived from Example 4). The desired single targeting sgRNA has been generated by in vitro transcription from a T7 promoter after linearizing the plasmid. The standard cloning vector pUC19 has been used as a target in our in vitro activity assays. A target site (20 nt+PAM) in the plasmid has been constructed by two complementary oligos which have been annealed and ligated into the sgRNA cloning vector. The produced sgRNA was incubated together with the Cas9 nuclease of T12 at temperatures ranging from 20° C. to 100° C. Cas9 cleavage activity has been assayed by agarose gel electrophoreses.

The organism isolated and characterised here (T12) has an optimum growth temperature of 65° C. which also represents the optimal temperature for its Cas9 protein. The temperature range in which it is active would be from 20° C. to 100° C., in particular 20° C. to 80° C.

The optimal temperature range of Cas9 from *Geobacilius* species is much higher than that of Cas9 proteins which have been characterised to date. Similarly the upper extent of the range in which it retains nuclease activity is much higher than that of known Cas9 proteins. A higher optimal temperature and functional range provides a significant advantage in genetic engineering at high temperatures and therefore in editing the genomes of thermophilic organisms, which have utility in a range of industrial, agricultural and pharmaceutical processes conducted at elevated temperatures.

What is claimed is:

1. A method of modifying a target nucleic acid comprising contacting the nucleic acid with
    a Cas protein having an amino acid sequence of SEQ ID NO: 1 or a sequence of at least 92% identity therewith and at least one targeting RNA molecule which recognizes the target sequence, wherein the targeting RNA molecule is a single guide RNA (sgRNA), further wherein the targeting RNA molecule is a single guide RNA (sgRNA) comprising a CRISPR RNA (crRNA) and a trans-activating small RNA (tracrRNA) linked by a synthetic loop.

2. A method of modifying a target nucleic acid in a cell, comprising transforming, transfecting or transducing the cell with:
    (i) an expression vector comprising a nucleotide sequence encoding comprising a nucleotide sequence encoding a Cas protein having an amino acid sequence of SEQ ID NO: 1 or a sequence of at least 92% identity therewith, and a further expression vector comprising a nucleotide sequence encoding a targeting RNA molecule which recognizes the target sequence, wherein the targeting RNA molecule is a single guide RNA (sgRNA), further wherein the targeting RNA molecule is a single guide RNA (sgRNA) comprising a CRISPR RNA (crRNA) and a trans-activating small RNA (tracrRNA) linked by a synthetic loop; or
    (ii) an expression vector comprising a nucleotide sequence encoding comprising a nucleotide sequence encoding a Cas protein having an amino acid sequence of SEQ ID NO: 1 or a sequence of at least 92% identity therewith and then delivering a targeting RNA molecule which recognizes the target sequence to or into the cell, wherein the targeting RNA molecule is a single guide RNA (sgRNA), further wherein the targeting RNA molecule is a single guide RNA (sgRNA) comprising a CRISPR RNA (crRNA) and a trans-activating small RNA (tracrRNA) linked by a synthetic loop.

3. A method of modifying a target nucleic acid as claimed in claim 1, wherein said Cas protein is fused to at least a further protein, wherein the at least one further protein comprises at least one functional moiety.

4. A method of modifying a target nucleic acid as claimed in claim 3, wherein the at least one functional moiety is a marker protein and the marker protein associates with the target nucleic acid.

5. A method of modifying a target nucleic acid as claimed in claim 3, wherein the target nucleic acid is dsDNA, the at least one functional moiety is a nuclease, and the modification is a single-stranded or a double-stranded break at a desired locus.

6. A method of modifying a target nucleic acid in a cell as claimed in claim 3, wherein the nucleic acid is dsDNA and the functional moiety is selected from the group consisting of a DNA modifying enzyme, a transcription activator or a transcription repressor, wherein the modifying of the target nucleic acid results in modification of gene expression in the cell.

7. A method of modifying a target nucleic acid in a cell as claimed in a method of claim 3, wherein the nucleic acid is an mRNA and the functional moiety is a ribonuclease and wherein the modifying of the target mRNA results in modification of gene expression in the cell.

8. A method of modifying a target nucleic acid in a cell as claimed in claim 2, wherein the method is carried out at a temperature between 50° C. and 100° C.

9. A method of modifying a target nucleic acid as claimed in claim 2, wherein the cell is a prokaryotic cell.

10. A method of modifying a target nucleic acid as claimed in claim 2, wherein the cell is a eukaryotic cell.

11. A method as claimed in claim 2, wherein the Cas encoding nucleotide sequence is covalently linked to a heterologous promoter sequence, and/or wherein the targeting RNA molecule is:
    (a) a single guide RNA (sgRNA) comprising a CRISPR RNA (crRNA) and
    (b) a trans-activating small RNA (tracrRNA) linked by a synthetic loop.

12. A fusion protein comprising:
    (a) a Cas protein having an amino acid sequence of SEQ ID NO: 1 or a sequence of at least 92% identity therewith, and
    (b) at least a further protein.

13. A fusion protein as claimed in claim 12, which is in the form of a ribonucleoprotein complex with at least one targeting RNA molecule, wherein the targeting RNA molecule is a single guide RNA (sgRNA), further wherein the targeting RNA molecule is a single guide RNA (sgRNA) comprising a CRISPR RNA (crRNA) and a trans-activating small RNA (tracrRNA) linked by a synthetic loop.

14. A fusion protein as claimed in claim 12, wherein the at least one further protein comprises at least one functional moiety.

15. A fusion protein as claimed in claim 14, wherein the at least one functional moiety is:
   (a) fused or linked to the N-terminus of the Cas protein; or
   (b) fused or linked to the C-terminus of the Cas protein; and further wherein the at least one functional moiety is a protein selected from the group consisting of a DNA binding protein, a DNA structuring protein, a marker protein, an affinity purification tag, a ligand binding protein, a signal peptide, and a subcellular localisation sequence.

16. A fusion protein as claimed in claim 12, wherein the native activity of the Cas9 nuclease is inactivated and the Cas protein is linked to at least one functional moiety selected from the group consisting of a nuclease domain, and a marker protein.

17. An isolated nucleic acid molecule encoding the fusion protein as claimed in claim 12.

18. An isolated nucleic acid molecule as claimed in claim 17, which is comprised within an expression vector.

19. An isolated nucleic acid molecule as claimed in claim 18, further comprising a nucleotide sequence encoding at least one targeting RNA molecule.

20. A fusion protein as claimed in claim 15, wherein:
   (a) the DNA binding protein is selected from the group consisting of a transcription activator or a transcription repressor;
   (b) the DNA structuring protein is selected from the group consisting of a helicase, a nuclease, a helicase-nuclease, a DNA methylase, a histone methylase, an acetylase, a phosphatase, a kinase;
   (c) the marker protein is selected from the group consisting of a reporter protein, a fluorescent protein, a ligand binding protein, a signal peptide, a subcellular localisation sequence;
   (d) the antibody epitope is an affinity purification tag.

21. A fusion protein as claimed in claim 16, wherein the at least one functional moiety is a FokI nuclease domain.

* * * * *